(12) United States Patent
Kaza et al.

(10) Patent No.: US 10,004,578 B1
(45) Date of Patent: Jun. 26, 2018

(54) SYSTEM FOR POST-PROCESSING ORTHODONTIC APPLIANCE MOLDS

(71) Applicant: Align Technology, Inc., San Jose, CA (US)

(72) Inventors: Srinivas Kaza, San Francisco, CA (US); Shiva P. Sambu, Mountain View, CA (US); Kamesh Tata, Santa Clara, CA (US); Michael J. Doung, El Cerrito, CA (US); Long Phan, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 190 days.

(21) Appl. No.: 14/297,393

(22) Filed: Jun. 5, 2014

Related U.S. Application Data

(60) Division of application No. 11/781,809, filed on Jul. 23, 2007, now Pat. No. 8,776,391, which is a
(Continued)

(51) Int. Cl.
*F26B 7/00* (2006.01)
*A61C 13/00* (2006.01)

(52) U.S. Cl.
CPC .................................. *A61C 13/00* (2013.01)

(58) Field of Classification Search
CPC ..... B65D 81/26; B65D 81/261–81/265; B65D 51/30; F26B 25/08; F26B 21/086;
(Continued)

(56) References Cited

U.S. PATENT DOCUMENTS 3,027,651 A 4/1962 Nerge
3,631,605 A * 1/1972 Wylie ..................... B29B 13/06
34/349
(Continued)

OTHER PUBLICATIONS

Office Action from USPTO dated Jun. 16, 2008 for related U.S. Appl. No. 11/781,809.
(Continued)

*Primary Examiner* — John McCormack
(74) *Attorney, Agent, or Firm* — Klein, O'Neill & Singh, LLP

(57) ABSTRACT

A system and method for post-processing of polymeric items having a liquid component and a predetermined heat deflection temperature is provided. The system includes a washing station to spray water at elevated temperature and pressure on the items while maintaining the temperature of the item below the heat deflection temperature. Then using a water distillation system to separate the water from the water mixed with the liquid polymer component by evaporating the water using heating coils with surface that is not conducive to adhesion of the liquid polymer component and then condense the water vapor into liquid water. The system may further include a spin station to separate the liquid polymer component by spinning the item. The system may further include one or more processing stations to rinse the item, dry the item, cure the item, remove the item from a tray to which the item may be attached and clean trays after removing the item. A conveyor system may be used to automate the post-processing of the items.

12 Claims, 11 Drawing Sheets

Related U.S. Application Data continuation of application No. 11/735,367, filed on Apr. 13, 2007, now abandoned.

(58) Field of Classification Search
CPC .............. H05K 5/0213; A61C 13/0013; A61C 13/0019; A61C 13/0027
USPC ... 34/381, 406–408, 202, 72–75, 79, 95, 85, 34/468, 312–316, 58; 433/201.1; 264/334–336, 339, 313, 317, 16–20, 163, 264/161, 138, 157, 37.3
See application file for complete search history.

(56) References Cited

U.S. PATENT DOCUMENTS

| | | | |
|---|---|---|---|
| 3,889,385 A * | 6/1975 | Dougherty | A61C 13/00 264/19 |
| 4,575,330 A | 3/1986 | Hull | |
| 4,685,551 A | 8/1987 | Ono et al. | |
| 4,832,753 A | 5/1989 | Cherry et al. | |
| 4,842,645 A | 6/1989 | Bettcher et al. | |
| 4,880,504 A | 11/1989 | Cellini et al. | |
| 5,112,916 A * | 5/1992 | Nakahashi | C08F 8/00 525/183 |
| 5,248,456 A * | 9/1993 | Evans, Jr. | B29C 67/0066 118/423 |
| 5,376,238 A | 12/1994 | Zambory | |
| 5,435,075 A | 7/1995 | Shiraishi et al. | |
| 5,480,607 A * | 1/1996 | Hobson | B29C 33/442 264/161 |
| 5,484,278 A * | 1/1996 | Berdan | B29C 45/1711 264/161 |
| 5,702,607 A | 12/1997 | Lawson | |
| 5,778,554 A | 7/1998 | Jones | |
| 5,791,984 A * | 8/1998 | Kane | F24F 13/08 219/201 |
| 5,899,216 A * | 5/1999 | Goudie | H01L 21/67028 134/134 |
| 6,004,047 A | 12/1999 | Akimoto et al. | |
| 6,017,397 A * | 1/2000 | Doran | B08B 7/0057 134/1 |
| 6,146,127 A * | 11/2000 | Foltuz | B29C 45/1771 264/334 |
| 6,190,165 B1 * | 2/2001 | Andreiko | A61C 7/16 433/9 |
| 6,341,431 B1 | 1/2002 | Noda | |
| RE37,627 E | 4/2002 | Hirano | |
| 6,848,568 B1 * | 2/2005 | Nibler | B65G 27/34 198/502.2 |
| 6,990,751 B2 | 1/2006 | Riley et al. | |
| 6,993,854 B2 | 2/2006 | Ise et al. | |
| 7,792,608 B2 | 9/2010 | Rice et al. | |
| 2003/0234179 A1 * | 12/2003 | Bang | B81C 99/0085 205/70 |
| 2004/0136881 A1 * | 7/2004 | Verser | B01J 4/008 422/132 |
| 2004/0222540 A1 * | 11/2004 | Weymouth, Jr. | B29D 11/00423 264/2.6 |
| 2005/0182229 A1 * | 8/2005 | Ibar | C08G 63/88 528/196 |
| 2006/0000109 A1 | 1/2006 | Lin et al. | |
| 2007/0173669 A1 * | 7/2007 | Sunkara | C08G 65/46 568/619 |
| 2007/0257387 A1 * | 11/2007 | Hofmann | B29D 11/00211 264/1.32 |
| 2009/0039558 A1 * | 2/2009 | Williams | E04B 2/14 264/336 |

OTHER PUBLICATIONS

Final Office Action from USPTO dated Nov. 25, 2008 for related U.S. Appl. No. 11/781,809.
Office Action from USPTO dated May 28, 2009 for related U.S. Appl. No. 11/781,809.
Final Office Action from USPTO dated Jan. 5, 2010 for related U.S. Appl. No. 11/781,809.
Office Action from USPTO dated Aug. 2, 2012 for related U.S. Appl. No. 11/781,809.
Final Office Action from USPTO dated Mar. 7, 2013 for related U.S. Appl. No. 11/781,809.
Office Action from USPTO dated Jul. 15, 2013 for related U.S. Appl. No. 11/781,809.
Notice of Allowance from USPTO dated Mar. 14, 2014 for related U.S. Appl. No. 11/781,809.

* cited by examiner

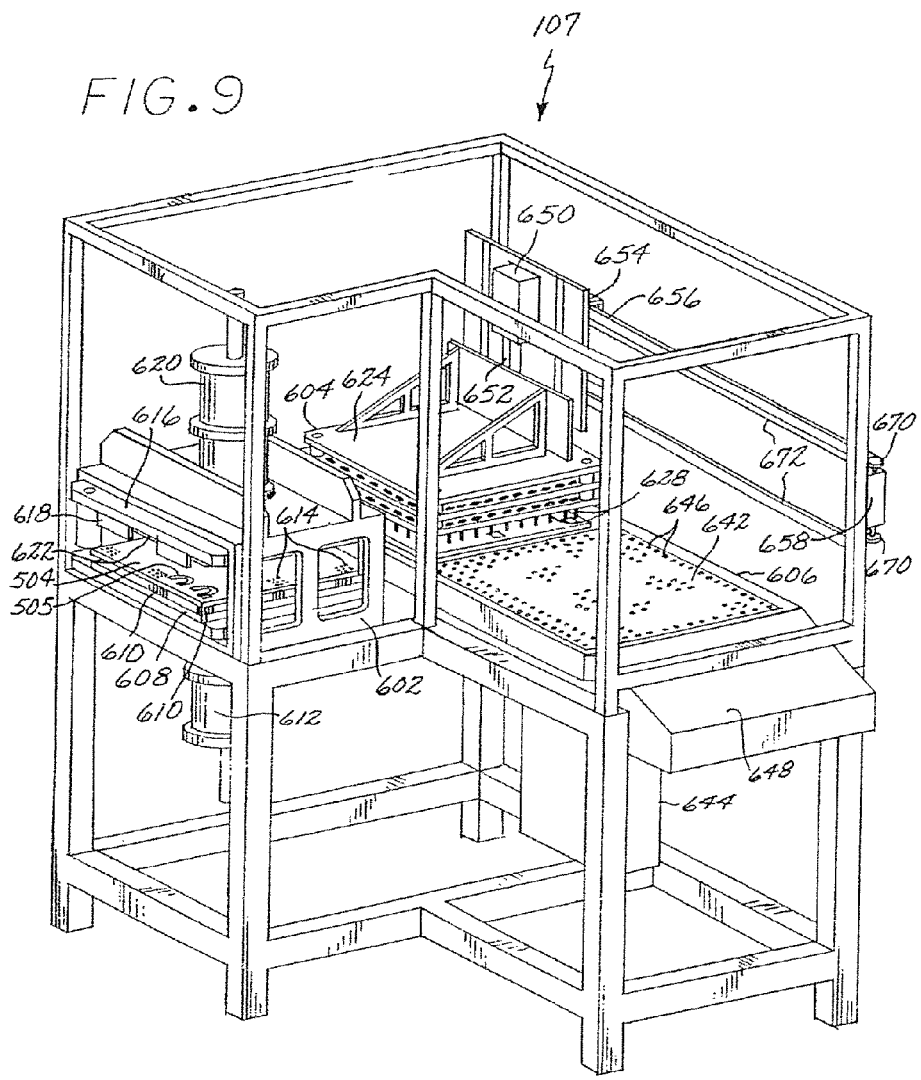

SYSTEM FOR POST-PROCESSING ORTHODONTIC APPLIANCE MOLDS

CROSS-REFERENCE TO RELATED APPLICATION

This application is a divisional of co-pending U.S. patent application Ser. No. 11/781,809, filed on Jul. 23, 2007; which is a continuation of U.S. patent application Ser. No. 11/735,367, filed Apr. 13, 2007, the disclosures of which are hereby incorporated herein by reference in their entireties.

FEDERALLY-SPONSORED RESEARCH OR DEVELOPMENT

Not Applicable

BACKGROUND OF THE INVENTION

1. Field of the Invention

This invention relates to the field of fabricating molds polymeric items, and more specifically, to an automated system for the post-processing of polymeric molds, particularly molds for fabricating plastic orthodontic appliances.

2. Background

Stereolithography is a rapid prototyping process used to create solid, plastic, three-dimensional (3-D) objects, such as molds, from CAD drawings. For example, stereolithography is used to fabricate molds that are used to make plastic orthodontic alignment appliances, as described, for example, in U.S. Pat. No. 5,975,893 and US Patent Application Publication 2005/0082703, both of which are commonly assigned to the assignee of the subject invention, and the disclosures of which are both incorporated herein by reference.

Plastic orthodontic appliances, of the type disclosed in the above-referenced documents, are made as a set of incremental position adjustment appliances that are used to realign or reposition a patient's teeth. The series of incremental position adjustment appliances is custom made for each patient during the fabrication process.

The fabrication process starts with a dentist making impressions or casts of the upper and lower dental arches of a patient. The impressions or casts are then sent by the dentist to an orthodontic appliance manufacturing facility. The manufacturing facility creates a treatment file from the impressions or casts that includes the treatment information for the patient. Treatment information includes the number of stages (i.e. each appliance in the series of incremental position adjustment appliances represents a stage) for both the upper and lower dental arches that are required for repositioning the patient's teeth, as well as how the patient's teeth move during each stage. The treatment file is then sent to the dentist for approval. Upon approval, the manufacturing facility generates 3D CAD models or images of molds for making the appliances using the treatment file, and then creates the molds using a rapid prototyping process, such as, for example, stereolithography. The molds are then used to fabricate the appliances.

Once the molds have been created, the molds are subjected to several post-processing steps. Currently, the post-processing of the molds is done manually, and includes removing any debris and any excess mold material (i.e., polymeric resin) from the molds. To clean the molds, they are first soaked in a solvent, and then they are sprayed with water and air to remove the excess resin and the loosened debris, and to rinse off the solvent.

The solvent used to clean the molds is toxic to the environment, and using fresh water to rinse off the solvent results in a significant consumption of water. Additionally, manually cleaning the molds is labor-intensive, and therefore entails substantial costs and time to produce the items. Accordingly, there is a need for an efficient system and method to improve productivity by automating the post-processing of the molds, using only water to clean the molds, and purifying the used water and waste resin from the molds to be reused.

SUMMARY OF THE INVENTION

As used herein, the terms "the invention" and "the present invention" shall encompass the specific embodiments disclosed herein, as well as any and all equivalents that may suggest themselves to those skilled in the pertinent arts.

In one aspect, the present invention is a system for removal of extraneous liquid material dispersed on an item, the system comprising a motor-driven platform having an axis of rotation and configured to removably hold the item radially displaced from the axis of rotation, wherein the platform is operable to rotate the item about the axis so as to separate the liquid from the item by centrifugal force while the item is held by the platform. In an exemplary embodiment of the invention, the items are polymeric molds for manufacturing plastic orthodontic appliances.

In a second aspect, the present invention is a system for post-processing of polymeric items having a liquid polymer component and a predetermined heat deflection temperature, the system comprising: a washing station operable to remove the liquid polymer component from the items, the washing station including a water spraying mechanism operable to spray water at elevated temperature and pressure on the items while maintaining the temperature of the items below the heat deflection temperature of the items and a water distillation system arranged to receive the portion of the mixture of water and the liquid polymer removed from the item by the washing station, and operable to separate by distillation the water from the liquid polymer in the mixture; wherein the distillation system comprises: a reaction chamber operable to maintain vacuum and having a heating coil operable to separate the liquid polymer and water by evaporating the water, wherein the heating coil has a surface that is not conducive to adhesion of the liquid polymer during the separation; and a condensation chamber arranged to receive water vapor from the reaction chamber and operable to condense the water vapor into liquid water. In an exemplary embodiment of the invention, the items are polymeric molds for manufacturing plastic orthodontic appliances.

In a third aspect, the present invention is a method for post-processing of polymeric items having a liquid polymer component and a predetermined heat deflection temperature, wherein the method comprises: spraying water at elevated temperature and pressure on the items while maintaining the temperature of the items below the heat deflection temperature of the items and removing liquid polymer from the items; receiving a mixture of water and the liquid polymer removed from the items and separating a portion of the mixture of water and the liquid polymer; separating the water from the liquid polymer in the mixture by distilling the mixture of water and the liquid polymer by subjecting the mixture of water and the liquid polymer to heat using heating coils not conducive to adhesion of the liquid during separation and under vacuum, and evaporating the water; and condensing the water vapor into liquid water.

In a fourth aspect, the present invention is a system for post-processing of polymeric items having a liquid polymer component, the system comprising: a motor-driven turntable having an axis of rotation and configured to removably hold the item radially displaced from the axis of rotation, wherein the turntable is operable to rotate the item about the axis so as to separate the liquid from the item by centrifugal force while the item is held by the turntable; a washing station operable to spray water at elevated temperature and pressure on the items to remove the liquid polymer component from the item; and a water distillation system arranged to receive a portion of the mixture of water and the liquid polymer removed from the item by the washing station and operable to separate by distillation the water from the mixture of water and the liquid polymer.

In a fifth aspect, the present invention is a for post-processing of polymeric items, the system comprising: a tray, the item attached to the tray by a sacrificial layer of the polymer; a detachment station operable to apply sufficient pressure to the item to separate the item from the tray by breaking the sacrificial layer; and a transfer plate including a plurality of movable pins, the transfer plate operable to position the movable pins to engage with the item and move the item relative to the tray. This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

The foregoing features and other features of the present invention will now be described with reference to the drawings of a preferred embodiment. In the drawings, the same components have the same reference numerals. The illustrated embodiment is intended to illustrate, but not to limit the invention. The drawings include the following Figures:

FIG. 9 is a perspective view of an exemplary removal station for use in the system of FIG. 1;

DETAILED DESCRIPTION OF THE INVENTION

The present invention provides a system and method for the processing, or "post-processing," of uncured polymeric resin items, such as, for example, dental appliance molds created by a rapid prototyping apparatus, such as a stereolithography apparatus (SLA). Post-processing includes one or more steps of removing any liquid or semi-liquid resin in or on the items after they are created, removing any debris and excess resin from the items, curing the items to increase their strength, removing the items and any excess support material from a tray or platform on which the items are held, and recovering any excess resin for reuse or disposal. The invention is described herein in the context of polymeric resin molds fabricated in an SLA. More specifically, the molds may be those used in the fabrication of plastic orthodontic appliances. Although the specific implementation of the fabrication of molds for plastic orthodontic appliances is described herein, the present invention can be utilized with any items created by SLA or other apparatus (especially rapid prototyping apparatus) used to make polymeric resin items.

In the above-mentioned specific implementation of the present invention for use with the fabrication of polymeric resin molds for plastic orthodontic appliances, a dentist makes a cast or an impression of a patient's upper and/or lower dental arches, and then sends the casts or impressions to an orthodontic appliance manufacturing facility. The manufacturing facility scans the casts or impressions (e.g., by CT scanning), and creates an electronic data or treatment file that includes the treatment information for the patient. The treatment information typically includes the scanned and digitized image of the cast or impression, the number of incremental positioning steps or "stages" for both the upper and lower dental arches that are required for each patient to reposition the patient's teeth, the position of the teeth in each stage, and how the teeth are moved between each successive stage.

The SLA builds a batch of items (such as molds) from polymeric resin, layer-by-layer, on a tray or platform. The tray or platform leaves or is removed from the SLA with the resin items on it in an uncured state, in which some of the resin may be in a liquid or semi-liquid state. In one embodiment, the item itself is substantially cured and some of the resin in a liquid or semi-liquid state is disposed on the item. Excess resin, in a liquid or semi-liquid state, may also be left on the tray or platform. At this point, the "post-processing" of the items may be commenced, in accordance with the present invention.

Figure 1:
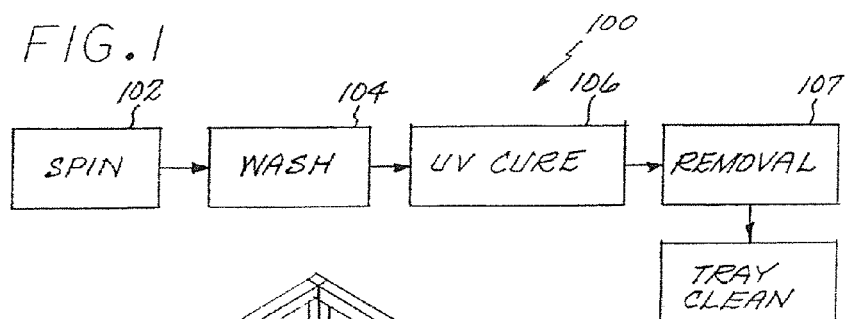
FIG. 1 is a block diagram of a system for processing polymeric resin items, such as polymeric molds, according to one aspect of the present invention.

FIG. 1 is a block diagram of a system 100 for automating the post-processing of items, particularly polymeric resin dental aligner molds, according to one aspect of the present invention. As mentioned above, the molds are built on a tray in the SLA. Once the molds have been completely built, the trays on which the molds are built are placed onto a conveyor belt or line (not shown) which transports the trays through different processing stations in the automated system 100 for performing multiple processes. Once the trays have completed all processes, the trays exit the system 100 onto an outgoing conveyor (not shown). One or more controllers (not shown), such as a programmable logic controller (PLC), controls the operation of the system 100.

The conveyor line first transports the trays to a spin station 102. The spin station 102 first detects that the trays have been loaded and locks the trays into place on a turntable. Once locked into place, the trays are subject to periods of rotation in both the clockwise and counter clockwise directions at speeds up to 500 RPM. The rotation forces any liquid or semi-liquid resin to flow off the molds and the trays by centrifugal force. The liquid or semi-liquid resin is then filtered and collected in a container for re-use. The spin station will be described later in detail, with reference to FIGS. 2, 3A, 3B, and 3C.

Upon completing the spin cycle, the trays are transported on the conveyor line to a washing apparatus 104 (described in detail below), which, in a preferred embodiment of the invention, is a closed-loop, high pressure, high temperature water spraying system. The high pressure water spray removes excess material, such as resin, from the items 505. Once the wash cycle is completed, the trays are transported to a high powered UV curing station 106 to cure the resin of the items 505. In the UV curing station 106, UV lamps (not shown) are advantageously reciprocated back and forth, exposing the items 505 to short doses of high-intensity UV radiation, instead of a single, long-term dose as is conventionally done.

From the UV curing station 106, the trays are transported to a mold and support removal station 107. The items 505 such as molds are attached to the tray with a sacrificial layer of the cured polymer. The removal station 107 applies sufficient pressure to the items 505 to break the sacrificial layer and separates the items 505 from the trays, without damaging the items 505. The removal station can further include a grinding plate to grind the items 505 to remove any excess sacrificial layer of the cured polymer and ensure a flat bottom, and presents the items 505 for example, molds for the next process in creating aligners.

From the mold and support removal station 107, the trays 504 (without the items) are transported to a tray cleaning station 108 where the tray 504 is cleaned by spraying water at high pressure to remove any polymeric resin material that is present on the tray. Cleaned trays are inspected and reused for the creation of the items, like the polymeric resin mold items.

Figure 2:
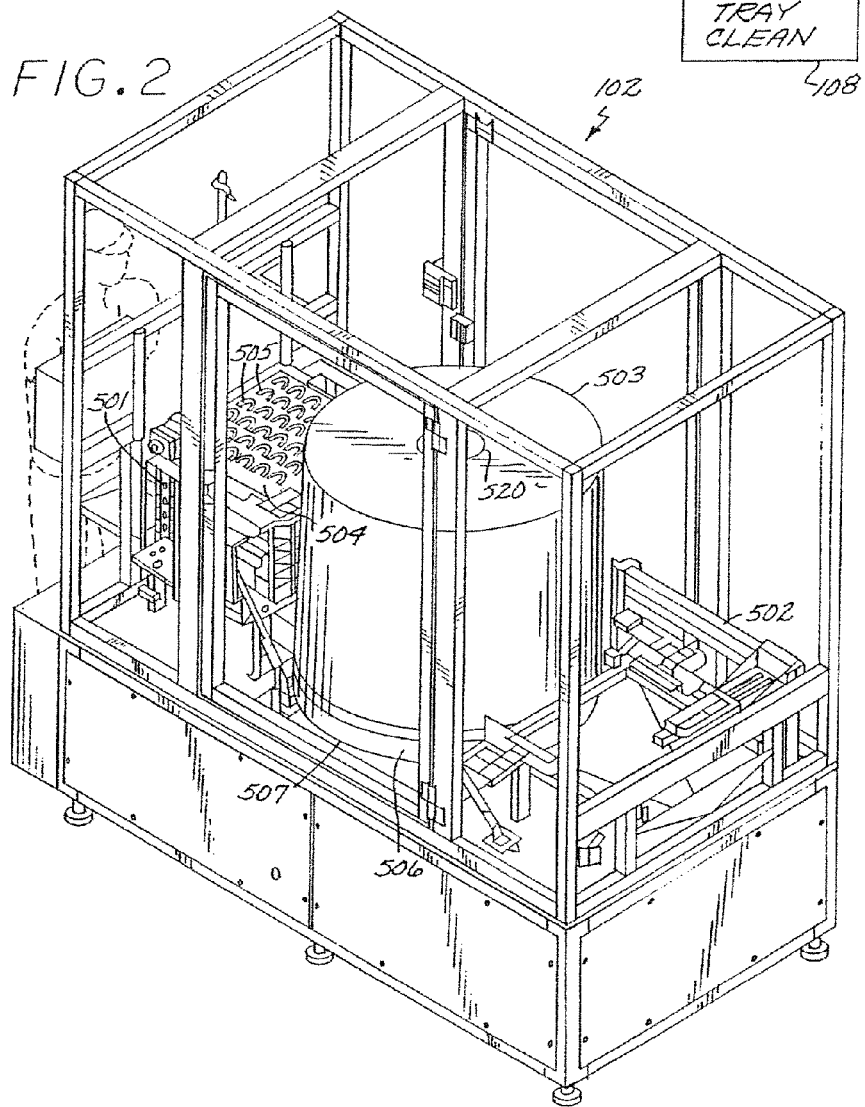
FIG. 2 is a perspective view of an exemplary spin station for use in the system of FIG. 1.

FIG. 2 shows an exemplary spin station 102. The spin station 102 includes a loading mechanism 501 that receives a tray 504 on which polymeric resin items 505, such as aligner molds, have been formed by means such as an SLA. The spin station further includes a spin chamber 507 to rotate the tray 504, and an unloading mechanism 502 to present the tray 504 after the tray 504 has been subject to rotation in the spin chamber 507. The spin chamber 507 includes a shroud 503, a turntable (not shown) and a collection bin 506. In one embodiment, the loading mechanism 501 may be configured to receive a plurality of trays 504 in a stacked arrangement, a lift mechanism to raise the trays 504 one at a time to a chamber loading position, and a load arm (not shown) operable to move the tray 504 from the loading position to a turntable in the spin chamber 507 as described below. The unloading mechanism 502 is operable to remove the tray 504 from the spin chamber 507 after the tray 504 has been subject to rotation.

The shroud 503 includes a top and a bottom portion and is configured to be movable from a closed position to an open position. In FIG. 2, the shroud 503 is shown in its closed position, surrounding the turntable configured to receive the tray and rotate the tray, details of which will be described in greater detail below, when further describing various aspects of the spin chamber 507. When the shroud 503 is in its closed position, the lower part of the bottom portion of the shroud 503 is inside the collection bin 506. When the shroud 503 is in its open position, access is permitted to the turntable for removable attachment of the tray to the turntable. In one embodiment, the inner wall of the shroud 503 is coated with a material conducive to permit the liquid polymer component that may be released from the items 505 and land on the inner wall of the shroud 503 to flow toward the bottom portion of the shroud 503 and drip into the collection bin 506 when the tray 504 is rotated. In another embodiment other parts of the spin chamber 507 may be coated with a material conducive to permit the liquid polymer component that may be released from the items 505 to slide down and drip into the collection bin 506. For example, the inner wall of the shroud and other parts of the spin chamber 507 may be coated with a PTFE compound such as TEFLON®, a material available from DuPont. In another embodiment, the side wall of the shroud 503 may be inclined inward from the top portion to the bottom portion so as to assist in the flow of the liquid toward the bottom portion of the shroud. In yet another embodiment, part of the bottom portion of the shroud may include an inwardly-tapered surface, which may further assist the flow of the liquid and permit the collection of the liquid in the collection bin 506. In one embodiment, the collection bin 506 may include a base and a side wall, with the side wall surrounding a portion of the bottom portion of the shroud 503 when the shroud 503 is in a closed position. The collection bin 506 may further include an outlet (not shown) to drain the liquid collected in the collection bin. The outlet (not shown) may be located in the side wall or the base of the collection bin 506. The base of the collection bin 506 may further be configured to be sloped toward the outlet (not shown), to permit the flow of the liquid toward the outlet of the collection bin 506. The collection bin 506 may further include an opening (not shown) to permit a turntable 509 (described below) to pass through the collection bin and rotate the tray 504.

Figure 3A:
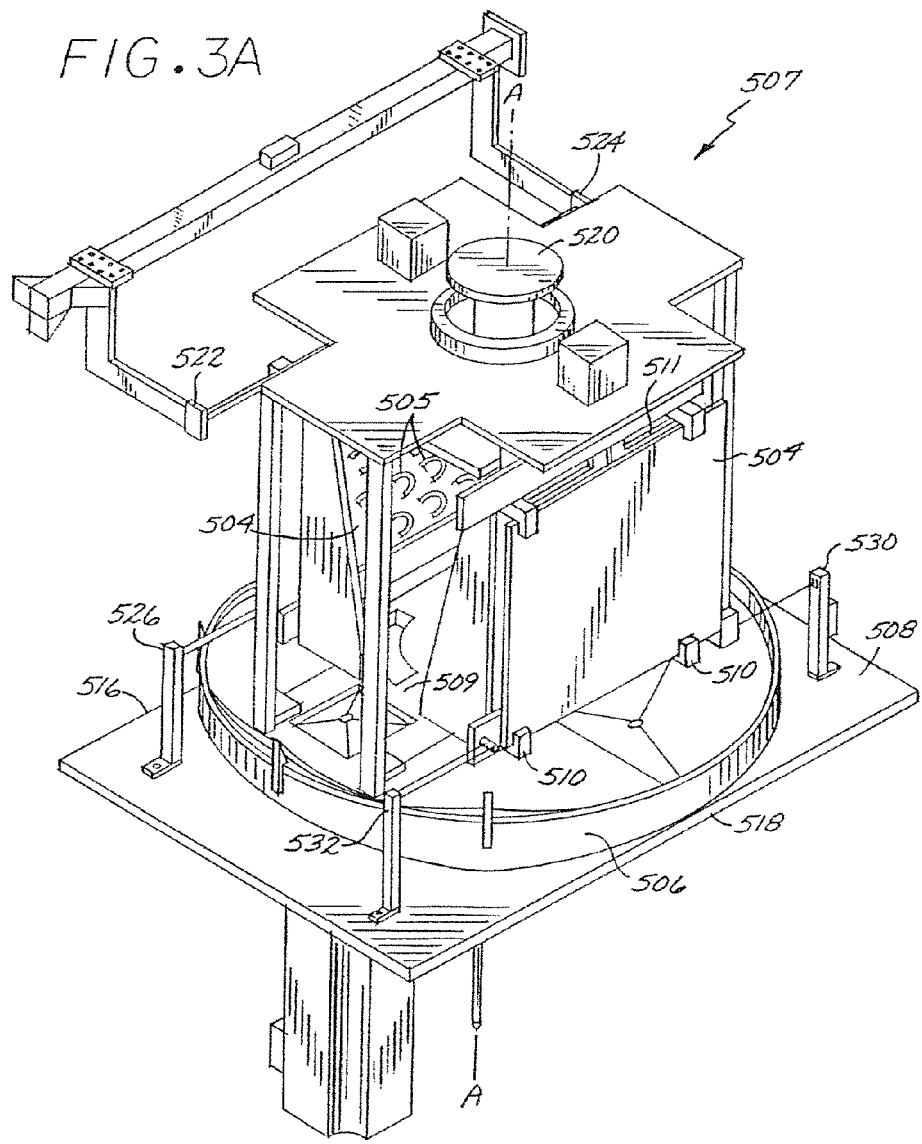
FIG. 3A is a perspective view of an exemplary spin chamber for use in the exemplary spin station of FIG. 2.

FIG. 3A shows an exemplary spin chamber 507 mounted on a platform 508 to which the collection bin 506 is attached. The platform 508 may also include frames and pillars to hold various transmitter/receiver pairs and provide rigidity to the spin chamber 507. The spin chamber 507 includes a turntable 509 that is operable to rotate about an axis A-A. A shroud plate 520 is coupled to an actuator (not shown) and moves along the axis A-A, when the actuator is actuated. The shroud 503 (not shown) is attached to the shroud plate 520 to move the shroud 503 from a closed position to an open position, by activating the actuator. In one embodiment, the turntable 509 is attached to a pulley (not shown) that is driven by a belt coupled to an electric motor (not shown). The turntable 509 is configured to receive the tray 504 from the loading mechanism 501 at a load side 516 of the spin chamber 507 and hold the tray 504 when the turntable 509 is rotated. The turntable 509 is further configured to permit the tray 504 to be moved to the unloading mechanism 502 at an unload side 518 of the spin chamber 507. The turntable 509 may include one or more position sensors (not shown) to determine the radial position of the turntable 509 in relation to a reference point. The position sensor(s) may be used to orient and position the turntable 509, for example, to receive the tray 504 from the loading station 501 at the load side 516 of the spin chamber 507. Similarly, the position sensor(s) may be used to orient and position the turntable 509 so as to permit the removal of the tray 504 to the unloading mechanism 502 at the unload side 518 of the spin station 507. The position sensor(s) may an include conventional optical and/or magnetic encoder assembly capable of sensing angular movement of the turntable 509, and the sensor(s) may be included in the motor driving the turntable 509.

In one embodiment, the turntable 509 is configured to removably hold the tray 504 in a position such that increased centrifugal force is applied to the item 505 when the turntable 509 is rotated. In an embodiment, the tray 504 is held radially offset from the axis of rotation A-A of the turntable 509. In an embodiment, the tray 504 is held in a vertical position radially offset from the axis of rotation A-A of the turntable 509, although tray 504 may be held in other orientations. The turntable 509 includes a pair of stationary clamps 510 and a movable clamp assembly 511 to removably hold the tray 504. The stationary clamps 510 hold the tray 504 near one of the edges of the tray 504 and the movable clamp assembly 511 holds the tray 504 near the edge opposite to the edges of the tray 504 held by the stationary clamps 510. The movable clamp assembly 511 is movable between an open position and a closed position. The detailed structure and operation of the movable clamp assembly 511 will be described below, with reference to FIG. 3B and FIG. 3C.

The spin chamber 507 may include several sensors to confirm the presence of the tray 504, the proper orientation of the tray 504, and the location of the turntable 509. In one embodiment, the spin chamber 507 on the load side 516 may include a sensor to confirm that the turntable 509 is properly aligned on the load side 516, to receive a tray 504 from the loading mechanism 501. This may, for example, be implemented by using one or more optical transmitter-receiver pairs 522,524 of a type well-known in the art. The optical transmitter and optical receiver pair are mounted on the platform 508 at positions corresponding to the proper alignment of the turntable 509 to receive a tray 504 from the loading station 501. The stationary clamp 510 on the turntable may include a through-hole that would permit the light beam transmitted from the optical transmitter to pass through the through-hole and reach the optical receiver only when the turntable 509 is properly oriented to receive the tray 504 from the loading mechanism 501. Similar optical transmitter-receiver sensor pairs 530, 532 can be mounted in the unload side 518 of the spin chamber 507 to indicate when the turntable 509 is properly aligned with the unloading mechanism 502, to unload the tray 504. Similar optical transmitter-receiver sensor pairs can be mounted on the platform 508 to confirm the presence of the tray 504 and to confirm that the tray 504 is not tilted.

Various parts of the turntable 509 are assembled using fasteners. In one embodiment, the fasteners are wire locked to ensure that various parts of the turntable 509 are held together and withstand the centrifugal force imparted on the turntable 509 during the operation of the spin station.

Figure 3B:
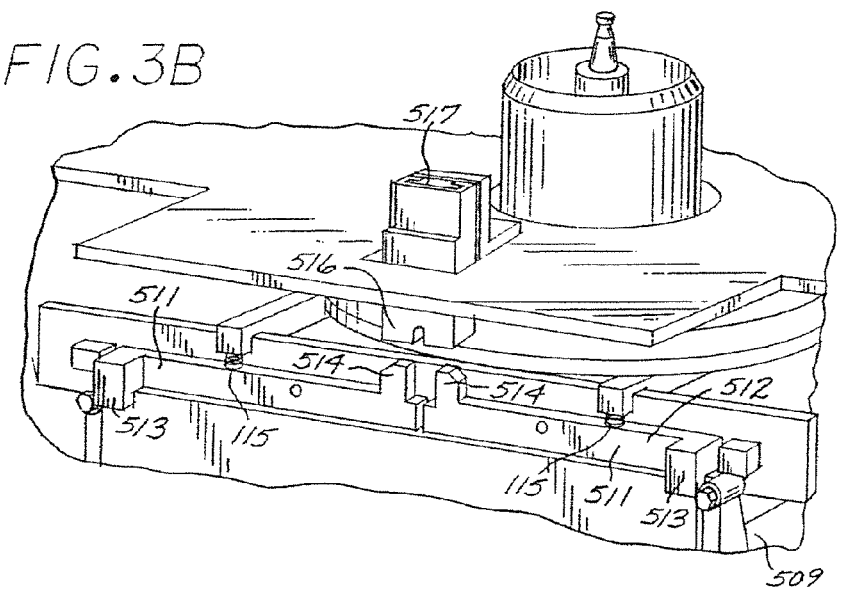
FIGS. 3B and 3C are detailed perspective views of an exemplary clamp assembly for use with the exemplary spin chamber of FIG. 3A.
Figure 3C:
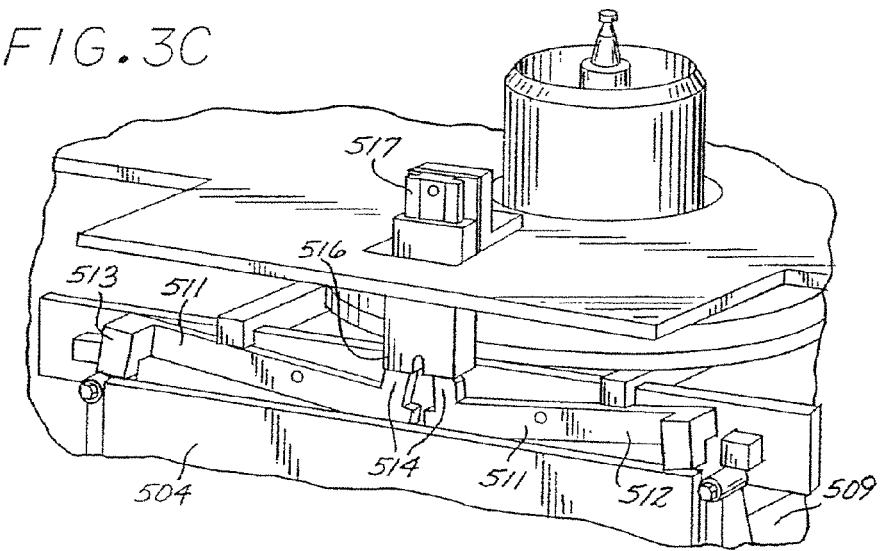

FIG. 3B shows the movable clamp assembly 511 in the closed position. FIG. 3C shows the movable clamp assembly 511 in the open position. The movable clamp assembly 511 includes a clamp arm 512 that is pivotally mounted on the turntable 509 so as to swing between an open position and a closed position. The clamp arm 512 further includes a clamp 513 at a distal end, configured to hold the tray 504 near the edges of the tray 504 when the clamp arm 512 is in closed position. The clamp arm 512 is biased by a spring 515 so that the clamp arm 512 is normally in the closed position. The clamp arm 512 further includes a head 514 at a distal end away from the clamp 513 so that a plunger 516 actuated by an actuator 517 may engage with the head 514 and swing the clamp arm 512 about the pivot to move the clamp arm 512 from the closed position to the open position.

The turntable 509 of the spin chamber 507 may be configured to receive one or more trays 504. When the turntable 509 is loaded, for example, with two trays, it may be advantageously loaded on both sides of the turntable 509, to assist in the balancing of the load on the turntable 509. The operating parameters of the turntable 509 may be different depending upon the number and characteristics of the tray 504 the turntable 509 is rotating. The turntable 509 is operable to rotate in both clockwise (CW) and counter-clockwise (CCW) directions, and it is further operable to accelerate to the desired rotational speed, and to decelerate therefrom to a stop at different rates ("ramp-up time" and "ramp-down time", respectively). It may also be operable to pause for a specified "dwell time" before restarting the rotation. The tray 504 may thus be subject to rotation both in the clockwise and counter-clockwise directions, for different spin times, rotational speeds, ramp-up times, ramp-down times, and dwell times, to achieve efficient removal of excess material.

In the preferred embodiment of the present invention, exemplary process parameters and limits for the turntable 509 are identified below, for a turntable rotating a single tray 504 and two trays 504. It should be noted that any suitable process parameters and limits may be used.

| Single Tray Cycle | Rotational Direction | RPM | Spin Time (seconds) | Ramp up time 0 to max RPM (seconds) | Rampdown time max RPM to 0 (seconds) | Dwell (seconds) |
|---|---|---|---|---|---|---|
| Spin1 | CW | 300 | 30 | 5 | 5 | 2 |
| Spin2 | CCW | 300 | 30 | 5 | 5 | 2 |
| Spin3 | CW | 300 | 30 | 5 | 5 | 2 |
| Spin4 | CCW | 300 | 30 | 5 | 5 | 2 |

| Two Tray Cycle | Rotational Direction | RPM | Spin Time (seconds) | Ramp up time 0 to max RPM (seconds) | Ramp down time max RPM to 0 (seconds) | Dwell (seconds) |
|---|---|---|---|---|---|---|
| Spin1 | CW | 400 | 30 | 5 | 5 | 2 |
| Spin2 | CCW | 400 | 30 | 5 | 5 | 2 |
| Spin3 | CW | 400 | 30 | 5 | 5 | 2 |
| Spin4 | CCW | 400 | 30 | 5 | 5 | 2 |

Figure 4:
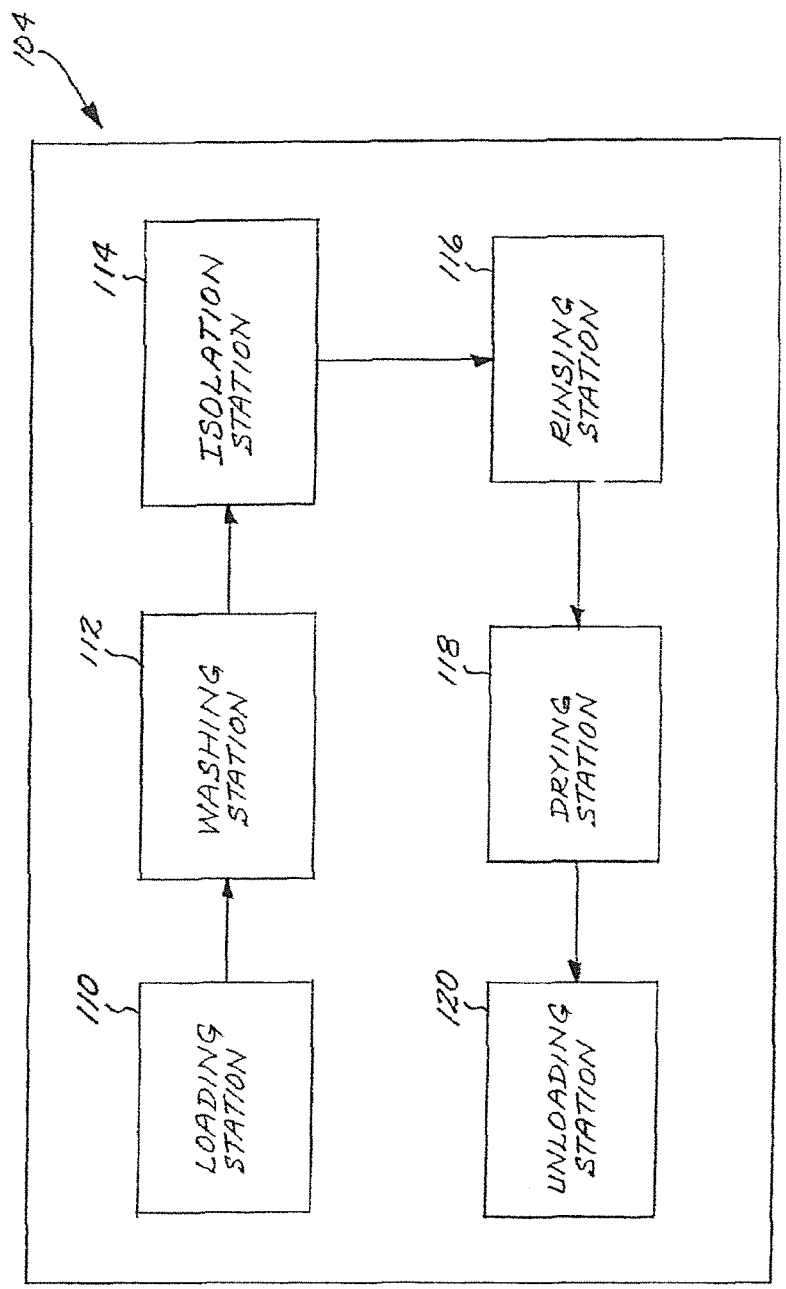
FIG. 4 is a block diagram of an exemplary embodiment of a washing apparatus for use in the system of FIG. 1.

FIG. 4 is a block diagram of an exemplary washing apparatus 104 for use in the system of FIG. 1. The conveyor line or belt transports the trays to a plurality of processing stations (described below) to perform a sequence of post-processing functions in a continuous fashion. For example, the conveyor line or belt may transport a tray 504 that has been processed through the spin chamber 507 and unloaded to the unloading mechanism 502. In the alternative, tray 504 may be manually loaded into the unloading mechanism 502. A sensor (not shown) may sense the presence of a tray 504 in the unloading mechanism 502 and transport the tray 504 to a plurality of processing stations (described below). The stations advantageously include the following: a loading station 110, a washing station 112, an isolation station 114, a rinsing station 116, a drying station 118 and an unloading station 120. The trays are transported from the spin station 102 first to the loading station 110. Once the trays are loaded, the conveyor line transports the trays to the washing station 112. As described in detail below, in the washing station 112 hot water is sprayed on the items as they pass through, thereby removing most of the excess resin from the items.

The conveyor line then transports the trays from the washing station 112 to the isolation station 114, where high pressure air blows any remaining water off of the molds. From the isolation station 114, the trays 504 are transported to the rinsing station 116, where any remaining residue, debris, or excess material is removed from the items by another hot water spray, as described below. As will be seen below, the rinsing station 116 may advantageously be substantially identical to the washing station 112, with the exception that the water sprayed onto the items is cleaner.

In the rinsing station 116, the trays and items accumulate water. To remove the accumulated water, the trays 504 are transported to the drying station 118. The drying station 118, as with the isolation station 114, uses high pressure air to blow off the excess water. Once the excess water is blown off, the trays 504 are transported to the unloading station 120 where the trays 504 are transferred to a downstream conveyor.

Figure 5A:
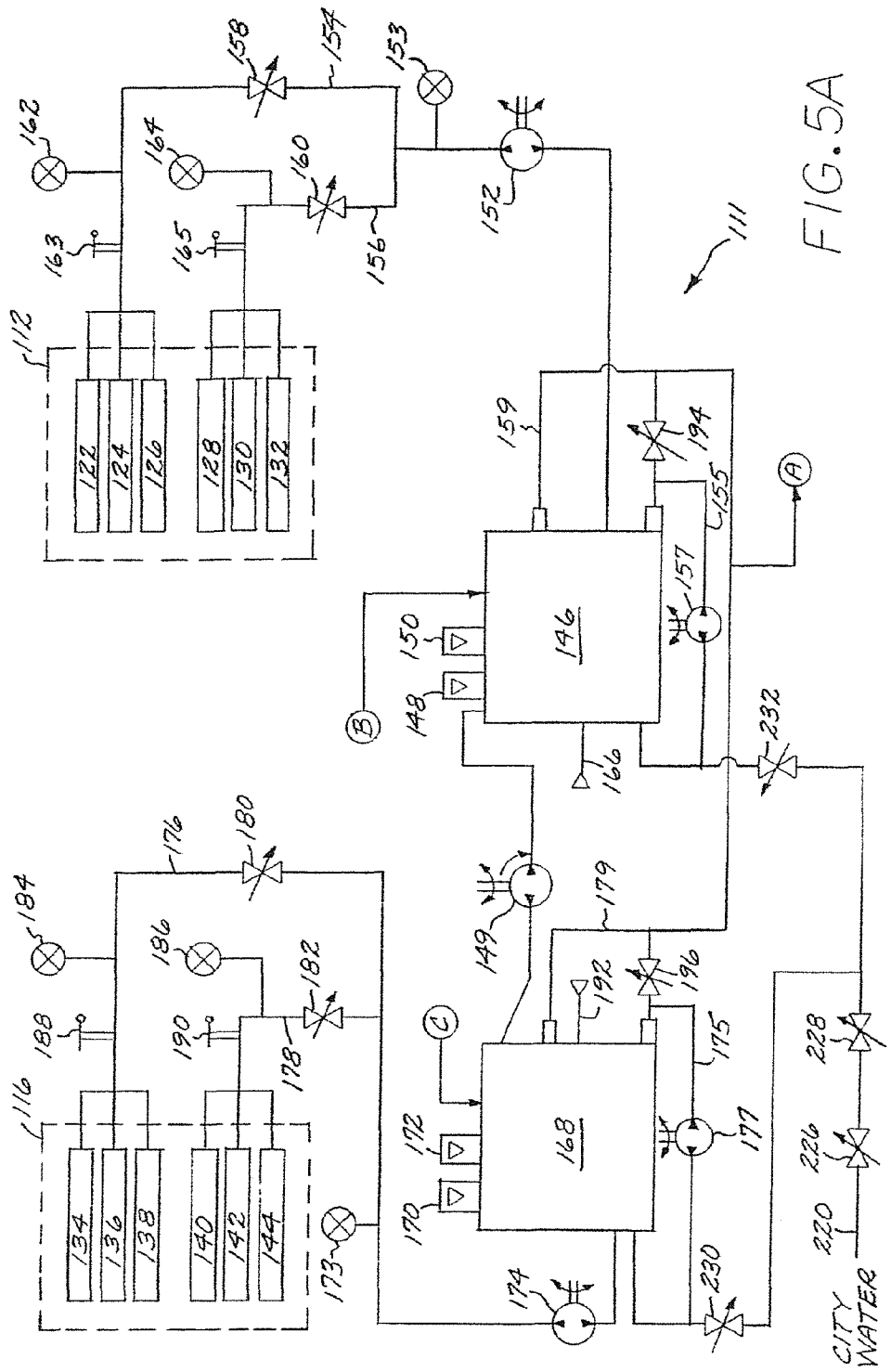
FIGS. 5A and 5B comprise a flow schematic of an exemplary washing apparatus for use in conjunction with the washing apparatus of FIG. 4.
Figure 5B:
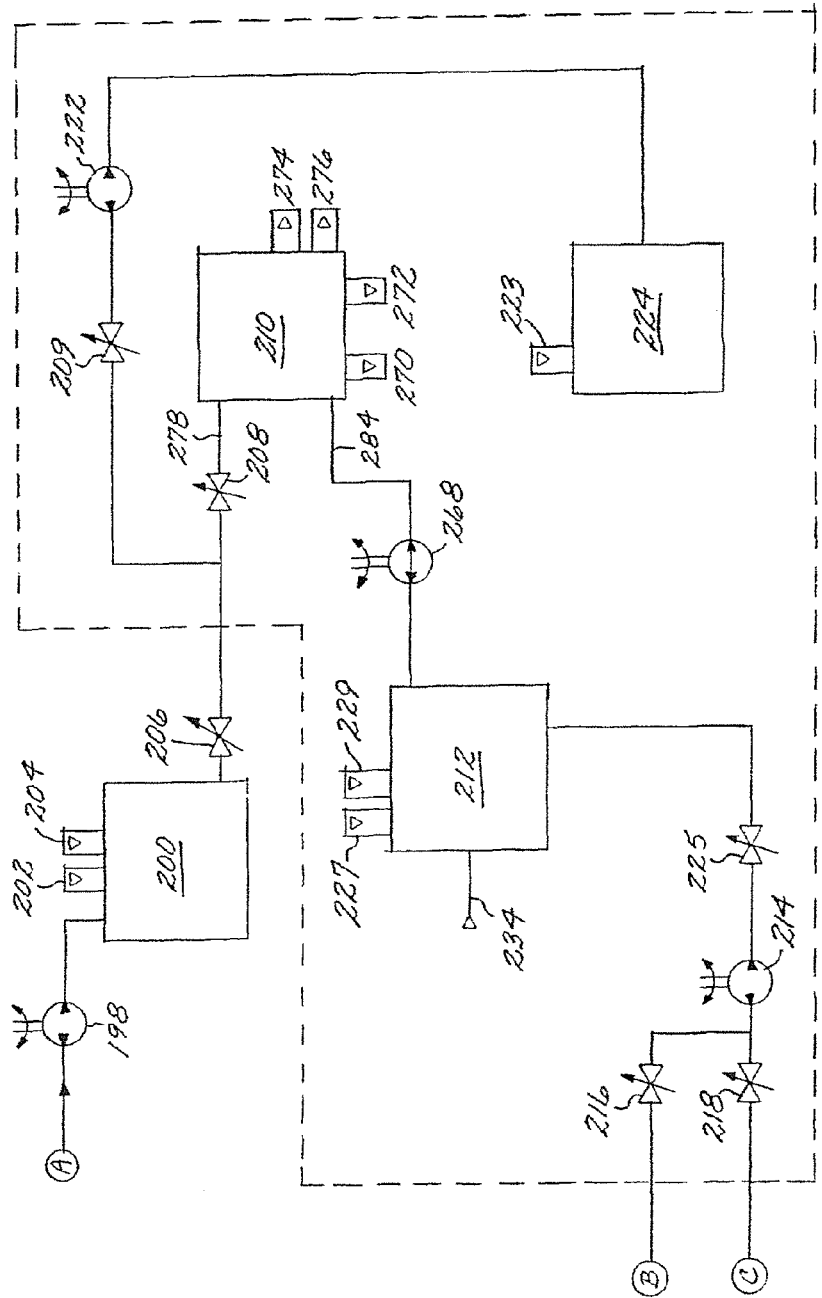

FIGS. 5A and 5B illustrate a flow schematic of a water filtering system 111, according to one aspect of the present invention. First, the trays 504 are transported on the conveyor line to the washing station 112 for removing excess resin. The washing station 112 has three top spray bars 122-126 and three bottom spray bars 128-132 for spraying water simultaneously onto the tops and bottoms, respectively, on the items 505 to wash off excess polymeric resin material from the items 505 on the trays 504. The washing station 112 may include an air handling system 290 operable to remove air mixed with water particles (which may further contain traces of polymeric resin materials) that may be formed in the washing station 112 when the water is sprayed under pressure on to the items 505. The air handling system 290 will be described in detail below. The water is maintained at an elevated temperature, e.g., in the range of about 110° F. (43° C.) to about 140° F. (60° C.), to enhance the removal of the excess material from the items 505. The temperature of the water is preferably maintained at such a level that the temperature of the item 505 is substantially maintained as close to but below the temperature at which the item 505 may deform to an extent where the item 505 may not be functionally useful. In one embodiment, the temperature of the water is preferably maintained at such a level that the temperature of the item 505 is substantially maintained as close to but below the heat deflection temperature of the material the item 505 is made of. In a preferred embodiment of the present invention, the temperature of the water used in the washing station 112 is maintained at about 130° F. (55° C.) and the pressure of the water is maintained at about 30 psi.

Figure 8:
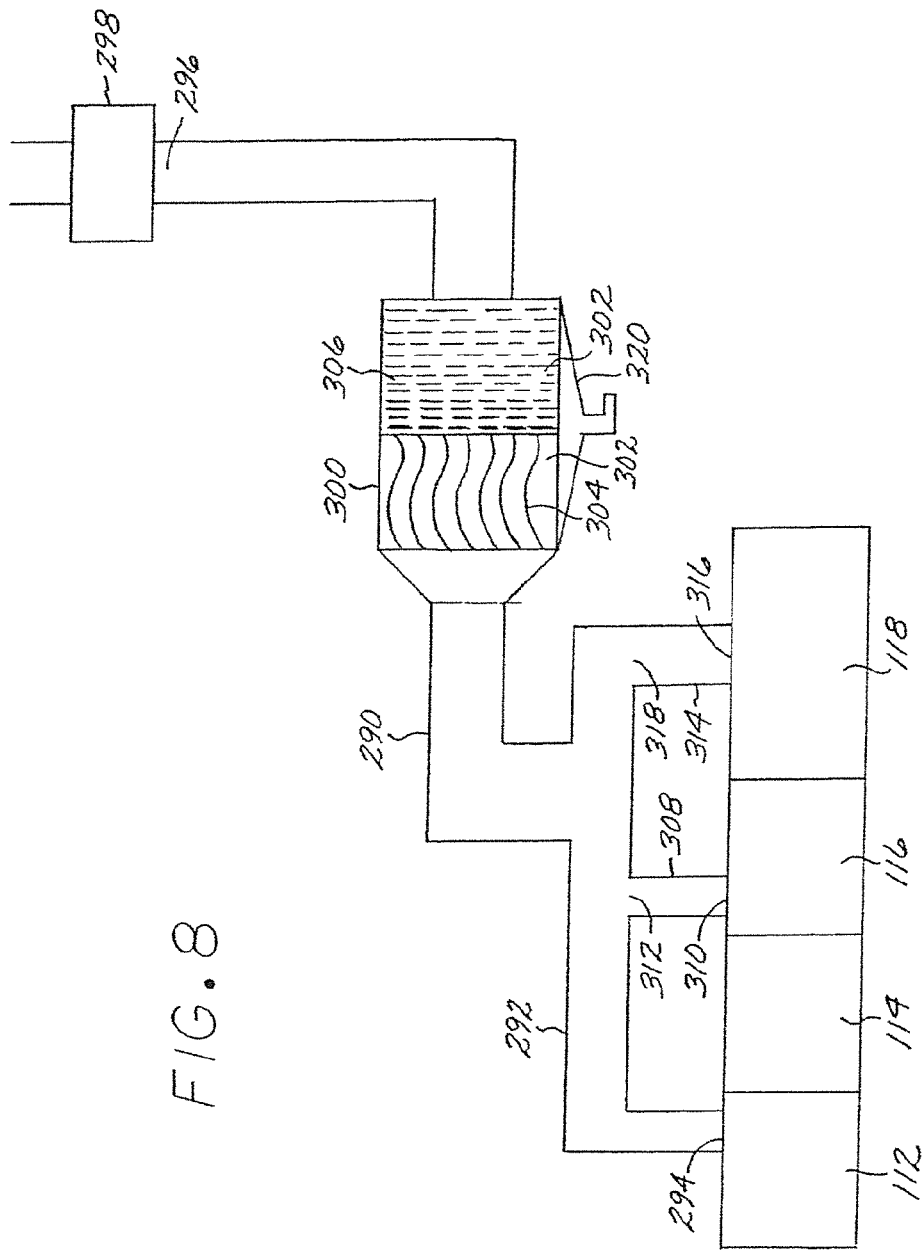
FIG. 8 is an air handling system for use with the washing apparatus of FIG. 4.

Now referring to FIG. 8, the air handling system 290 includes a duct with an inlet 294 and an outlet 296, and a blower 298. The blower 298 is connected to the outlet 296 of the air handling system 290 to draw the air mixed with water particles (which may contain traces of polymeric resin material) from the inlet 294, toward the outlet 296. In one embodiment, a mist removal station 300 may be connected to the duct 292, between the inlet 294 and the outlet 296 to separate water particles (which may further contain traces of polymeric resin material) contained in the air mixed with water particles. The air handling system 290 when operational, maintains a negative air pressure in the vicinity of the inlet 294 to assist in the removal of the air mixed with water particles formed in the washing station 112, toward the outlet 296. The mist removal station 300 may include one or more separation stations 302 to separate the water particles from the air water mixture. One or more separation stations 302 may be connected in series to pass the air mixed with water particles through successive separation stations. In one of the separation station 302, air mixed with water particles are passed over plates 304 that are curved. For example, the plates may be chevron shaped. The plates may be made of stainless steel. The plates may be separated by a gap of about one inch to three inches, preferably about one and a half inches to permit the flow of air mixed with water. When the air mixed with water particles flows over the curved plates, water particles settle on the surface of the plates. Water particles collected on the plates flow toward the edges of the plates and are collected in the collection chute 320 and fed to the water filtering system 111, which will be described in detail later. In one embodiment, the mist removal station 300 may include another separation station 302 with one or more mesh 306 with fine pores through which the air mixed with water particles pass through. In one embodiment, the fine pores in the mesh 306 may be of the order of 200 microns. In one embodiment, the mesh 306 may be made of stainless steel. In one embodiment, multiple meshes 306 may be packed together to form a thick pack of mesh 306. The thickness of the pack of mesh 306 may be in the range of about two inches to about 12 inches, preferably, about six inches. Any water particles trapped in the mesh 306 will flow down and are collected in the collection chute 302 and fed to the first holding tank 200 of the water filtering system 111, which will be described in detail later.

From the washing station 112, the trays are transported on the conveyor line to the isolation station 114 (see FIG. 4). The isolation station 114 uses high pressure air to blow off the water from the items 505. From the isolation station 114, the trays 504 are transported to the rinsing station 116. The rinsing station 116, as with the washing station 114, has three top rinse spray bars 134-138 and three bottom rinse spray bars 140-144 for spraying water onto the items to remove excess resin not removed in the washing station 112.

Now referring back to FIG. 7, the rinsing station 116 may further include a second air handling system similar to the air handling system 290 as previously discussed. For example, the inlet 310 of a second duct 308 may be connected to the rinsing station 116 and the outlet of the second duct 312 may be connected to a second blower (not shown) to draw air mixed with water particles (which may further contain traces of polymeric resin material) in the rinsing station 116 from the inlet 310 of the second duct 308 toward the outlet of the second duct. In the alternative, the inlet 310 of the second duct 308 may be connected to the rinsing station 116 and the outlet 312 of the second duct connected to the duct of the air handling system 290 between the inlet 294 and the outlet 296 of the duct 292 of the air handling system 290, so that the blower 298 of the air handling system 290 can be used to draw air mixed with water particles from the rinsing station 116 through the inlet 310 of the second duct 308 toward the outlet 296 of the duct 292 of the air handling system 290. The air handling system 290 when operational, maintains a negative air pressure in the vicinity of the inlet 310 of the second duct 308 to assist in the removal of the air mixed with water particles formed in the rinsing station 116, toward the outlet 296 of the duct 292.

Similarly, a third duct 314 may be connected to the drying station 118 to draw air mixed with water particles (which may further contain traces of polymeric resin material) from the drying station 116. The inlet 316 of the third duct 314 may be connected to the drying station 118 and the outlet 318 of the third duct 314 connected to the duct 292 of the air handling system 290 between the inlet 294 and the outlet 296 of the duct 292 so that the blower 298 of the air handling system 290 can be used to draw air mixed with water particles from the drying station 118 through the inlet 316 of the third duct 314 toward the outlet 296 of the duct 292 of the air handling system 290. The air handling system 290 when operational, maintains a negative air pressure in the vicinity of the inlet 316 of the third duct 314 to assist in the removal of the air mixed with water particles from the drying station 118, toward the outlet 296 of the duct 292. As one skilled in the art would appreciate, the diameter of the ducts 292, 308 and 314 and inlets 294, 310 and 316 are suitably selected to permit efficient removal of proper quantity of air mixed with water particles (which may further contain traces of polymeric resin material). For example, in one embodiment, the diameter of the inlet 316 in the drying station 118 may be advantageously be bigger than the diameter of the inlets 294 and 310.

In the preferred embodiment, the water used in the rinsing station 116 is cleaner than the water used in the washing station 112, as the cleaner water removes the final amount of residue on the molds. The water is maintained at an elevated temperature to enhance the removal of the excess material from the item. The temperature of the water is preferably maintained at such a level that the temperature of the item 504 is maintained as close to but slightly below the heat deflection temperature of the material from which the molds are made. In a preferred embodiment of the present invention, the temperature of the water used in the rinsing station 116 is maintained at about 130° F. (55° C.), and the pressure of the water is maintained at about 30 psi. A wash tank 146 supplies water to the top and bottom spray bars 122-132 in the washing station 112 and collects the contaminated water (i.e. the water mixed with resin) for later filtration. The wash tank 146 is heated, preferably by an internal heater (not shown), or alternatively by an external heat source (not shown), to maintain the desired elevated water temperature. A first wash tank level sensor 148 and a second wash tank level sensor 150 monitor the water level in the wash tank 146 to ensure that there is sufficient water for the washing station 112. A water tank pump 152 is used to pump the water from the wash tank 146 to the top and bottom wash spray bars 122-132. The water from the wash tank 146 is split into a top spray bar line 154, for supplying water to the top wash spray bars 122-126, and a bottom spray bar line 156 for supplying water to bottom wash spray bars 128-132. A water tank pressure gauge 153 measures and visually displays the pressure of the water exiting the water tank pump 152 for an operator to view.

A first wash pressure sensor 163 measures the pressure in the top spray bar line 154, and a second wash pressure sensor 165 measures the pressure in the bottom spray bar line 156. A first pressure gauge 162 visually displays the pressure in the top spray bar line 154 and a second pressure gauge 164 visually displays the pressure in the bottom spray bar line 156. The pressure sensors 163, 165 transmit, either continuously or at frequent intervals, the measured values to the PLC. If a value is at an inappropriate level, the PLC can take the appropriate steps to correct the problem.

A thermocouple 166, operatively associated with the wash tank 146, measures the temperature of the water therein. A thermocouple with dual sensing elements may be used for increasing the accuracy of the water temperature measurement. A substantially constant volume of water must be maintained in the wash tank 146 at a substantially constant temperature. Accordingly, the thermocouple 166 and the first and second wash tank level sensors 148, 150 send their measured values to the PLC, either continuously or at frequent intervals. If the measured values are not within the desired ranges, the PLC can take the appropriate steps to restore the proper water level in the wash tank 146 and/or to adjust the water temperature by controlling the water tank heater. Additionally, the water in the wash tank 146 may be recirculated using a wash tank recirculation pipe 155 and a wash tank recirculation pump 157. The water in the wash tank 146 may be recirculated using the recirculation pump 157 to minimize water temperature gradient within the wash tank 146.

A rinse tank 168 supplies water to the top and bottom rinse spray bars 134-144 in the rinsing station 116 and collects the contaminated water for later filtration. The rinse tank 168 is heated by means similar to that described above for the wash tank 146, to maintain the water therein at a suitable elevated temperature. A transfer pump 149 may be employed to pump water from the wash tank 146 to the rinse tank 168, or vice versa. A first rinse tank level sensor 170 and a second rinse tank level sensor 172 monitor the water level in the rinse tank 168 to ensure that there is sufficient water for the rinsing station 116. A rinse tank pump 174 is used to pump water from the rinse tank 168 into a top rinse spray bar line 176, for supplying water to the top spray bars 134-138, and a bottom rinse spray bar line 178 for supplying water to bottom spray bars 140-144. A rinse tank pressure gauge 173 measures and visually displays the pressure of the water and also transmits a signal to the PLC to take corrective action if the water pressure is too high or too low.

A first rinse pressure sensor 188 measures the pressure in the top rinse spray bar line 176 and a second rinse pressure sensor 190 measures the pressure in the bottom rinse spray bar line 178. A first rinse pressure gauge 184 visually displays the pressure in the top rinse spray bar line 176 and a second rinse pressure gauge 186 visually displays the pressure in the bottom rinse spray bar line 178. The sensors 188, 190 transmit the measured values, either continuously or at frequent intervals, to the PLC. If a value is not within the desired range, the PLC can take the appropriate steps to correct the problem.

A rinse tank thermocouple 192, operatively associated with the rinse tank 168, measures the temperature of the water. A thermocouple with dual sensing elements may be used for increasing the accuracy of the temperature measurement. A substantially constant level of water must be maintained in the rinse tank 168 at a substantially constant temperature. Accordingly, the thermocouple 192 and the first and second rinse tank level sensors 170, 172 send their values to the PLC, either continuously or at frequent intervals. If the measured values are not within the desired ranges, the PLC can take the appropriate steps to restore the proper water level and/or to adjust its temperature by controlling the rinse tank heater. Additionally, the water in the rinse tank 168 may be recirculated using a rinse tank recirculation pipe 175 and a rinse tank recirculation pump 177. The water in the rinse tank 168 may be recirculated using the rinse tank recirculation pump 177 to minimize water temperature gradient within the rinse tank 168.

For example, when there are no items 505 to be processed through the system, it may be advantageous to stop the operation of various pumps and circulation of water through the system, however, the water in the wash tank 146 and the rinse tank 168 may be advantageously be recirculated using the recirculation pump 157 and 177 while keeping the heater on in the wash tank 146 and the rinse tank 168. The recirculation of the water in the wash tank 146 and the rinse tank 168 may advantageously minimize the water temperature gradient in the wash tank 146 and the rinse tank 168 so that the water is accurately maintained at the elevated temperature and there is minimal startup time to initiate the cleaning operation once the items 505 are available for cleaning in the washing station 112 and the rinsing station 116.

To purify the contaminated water (including the resin) collected in the wash tank 146 and the rinse tank 168, the water from the tanks is removed by manually opening a wash tank valve 194 and a rinse tank valve 196. During normal operation of the washing station 112 and the rinsing station 116, the manual water tank valve 194 and the rinse tank valve 196 are in their open position. A holding tank pump 198 then pumps the water into a first holding tank 200 (FIG. 5B) having a sloped bottom for collecting the resin. In addition, a portion of the resin rises to the top of the wash tank 146 and the rinse tank 168 and forms a resin foam. The wash tank 146 and the rinse tank 168 are configured such that the resin foam along with water is removed from the wash tank 146 and the rinse tank 168 and collected in the first holding tank 200. Specifically, in one embodiment, the wash tank 146 and the rinse tank 168 are provided with overflow pipes 159, 179 connected to the first holding tank 200. By maintaining an excess flow of water into the wash tank 146 and the rinse tank 168, the excess water flowing into the wash tank 146 and the rinse tank 168 can advantageously remove the resin foam from the wash tank 146 and the rinse tank 168 through the overflow pipes 159, 179 to the first holding tank 200. The first holding tank 200 is advantageously provided with at least one water level sensor (not shown) for monitoring the water level therein and generating a water level signal that may advantageously be used to control the flow of water and the operation of the system. A portion of the resin that has been removed from the items and mixed with the water settles on the bottom of the holding tank 200, as resin is denser than water. The resin that has settled on the sloped bottom of the first holding tank 200 is periodically removed and may be re-used or disposed off properly. In addition, a portion of the resin that has been removed from the items and mixed with the water may not settle on the bottom of the holding tank 200, as for example, the resin foam that floats on the top of the wash tank 146 and the rinse tank 168. The water mixed with the resin foam is further processed in the distillation system 210, as described in detail below.

Referring to FIG. 5B, from the first holding tank 200, contaminated water passes through a manual valve 206, and then flows through one of two different routes. In the first route, a distillation valve 208 is opened causing the water to flow into a distillation system 210 where the water is evaporated under a vacuum (as opposed to under atmospheric pressure). The benefit of evaporating under vacuum is that any liquid, including water, evaporates at a lower temperature than at ambient (atmospheric) pressure. Thus, in the distillation system 210 of the present invention, evaporation takes place at room temperature. The water flows to the distillation system 210 from the first holding tank 200 due to vacuum maintained in the distillation system 210, and a pump is not needed. The valves 206 and 208 are in open position during the normal operation of the distillation system 210.

The evaporated water vapor from the distillation system 210 is condensed in a separate tank within the distillation system 210 (described below with reference to FIG. 6). For a period of time, the distillation system 210 is constantly evaporating contaminated water and then retrieving purified water from the vapor. The contaminants (e.g. resin) from the water fall to the bottom of the tanks and are gradually removed.

The purified water from the distillation system 210 is collected in a second holding tank 212. A first water level sensor 227 and a second water level sensor 229 indicate the water level inside the second holding tank 212. Signals from these sensors may advantageously be used to control the flow of water into and out of the second holding tank 212. A thermocouple 234, operatively associated with the second holding tank 212, measures the temperature of the water therein.

Upon opening a second holding tank outlet valve 225, a holding tank pump 214 pumps the water out of the second holding tank 212, as needed, to replenish water in the wash tank 146 and the rinse tank 168. If water from the second holding tank 212 is transferred to the wash tank 146, a first transfer valve 216 is opened, allowing the water to flow into the wash tank 146. If the water from the second holding tank 212 is transferred to the rinse tank 168, a second transfer valve 218 is opened, allowing the water to flow into the rinse tank 168. During normal operation of the distillation system 210, the valves 216, 218 and 225 are in their open position.

Referring again to FIG. 5A, water (preferably from a municipal or private water line 220) is processed through a water softener to remove minerals that may be harmful to the operation of the system and then fed into the rinse tank 168 and the wash tank 146 when a pair of main valves 226, 228 and a pair of tank-filling valves 230, 232 are opened. The default position of the tank-filling valves 230, 232 is open. The water that is being used is at a high temperature, around 130° F. (55° C.), and thus there is a constant water loss in the form of water vapor. To compensate for the loss, the water from the line 220 may be used to fill the tanks 146, 168.

In the second route from the first holding tank 200, a bypass valve 209 is opened, causing the water to bypass the distillation system 210. This is typically done when maintenance on the system is required. During maintenance, the water is drained from the system so that the system can be cleaned. A drain pump 222 pumps water from the first holding tank 200 to a third holding tank 224. A third holding tank water level sensor 223 communicates with the PLC. If the water level in the third holding tank 223 reaches tank capacity, the PLC automatically closes the bypass valve 209, preventing the third holding tank 224 from overflowing.

Figure 6:
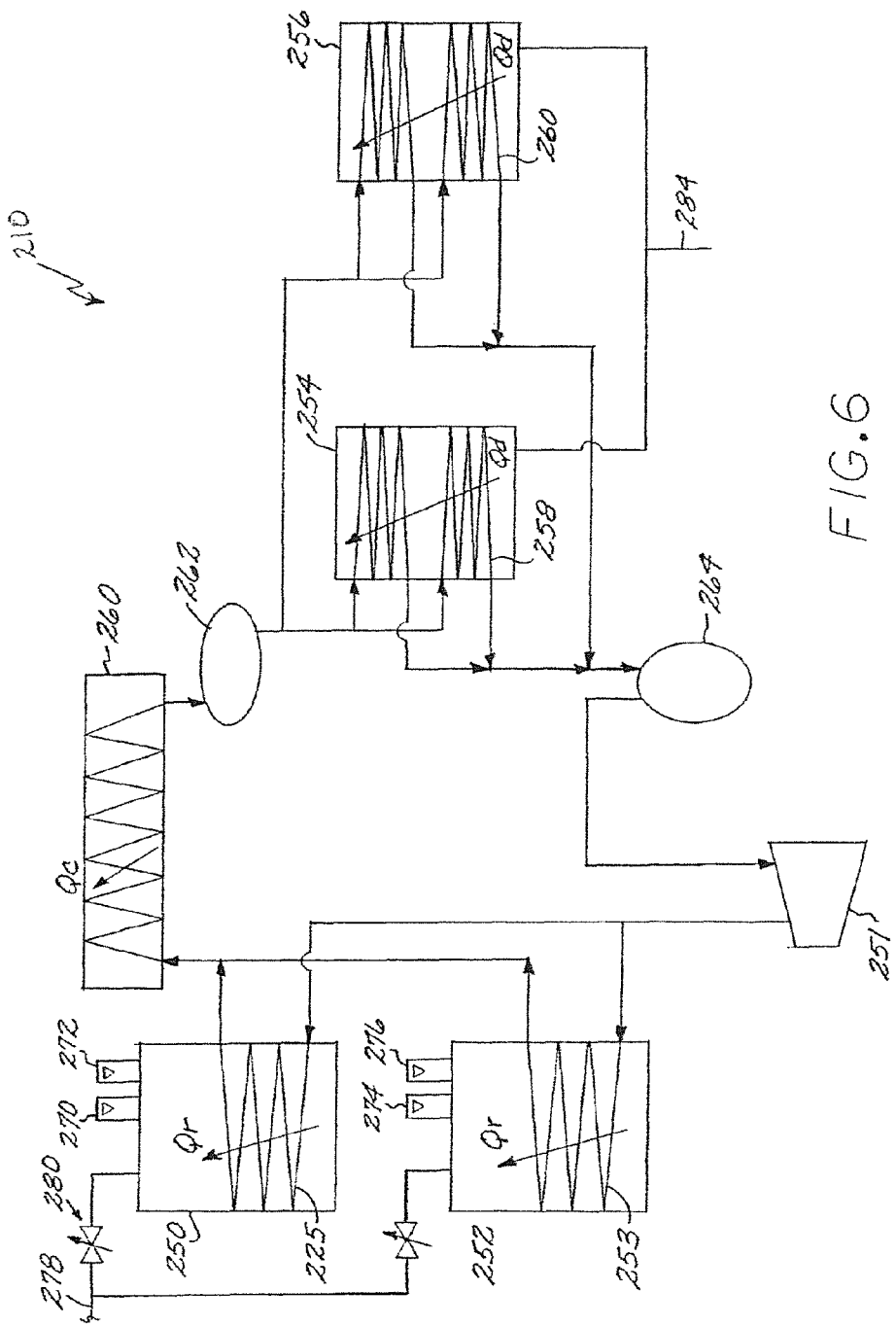
FIG. 6 is a block diagram of an exemplary distillation system for use in the water filtration system shown in FIG. 5B.

FIG. 6 is a block diagram of the distillation system 210 of FIG. 5B. The distillation system 210 is a closed-loop filtration system that purifies water from the system 100 for automating the post-processing of items. In the distillation system 210, the contaminated water is fed into a first reaction chamber 250 and a second reaction chamber 252. The water is evaporated using heat in the first reaction chamber 250 and the second reaction chamber 252, and then it is cooled in a first product chamber 254 and a second product chamber 256 through a standard refrigeration process. Although the system is described with two reaction chambers and two product chambers, a system can be advantageously built using a single reaction chamber and a single product chamber.

A compressor 251 is used to heat a refrigerant, and the heated refrigerant is fed into the first reaction chamber 250 and the second reaction chamber 252 through a first reaction coil 253 and a second reaction coil 255, respectively. The contaminated water in the first reaction chamber 250 and the second reaction chamber 252 boils when it comes in contact with the hot refrigerant-filled reaction coils 253, 255, causing the contaminated water to evaporate at low temperature under vacuum (achieved with a vacuum pump, not shown). This process leaves a resin residue in the first reaction chamber 250 and the second reaction chamber 252. The outer surfaces of the first reaction coil 253 and the second reaction coil 255 are made of a material or coated with a material that can withstand the high temperature and that is not conducive to adhesion of the resin residue. In one embodiment, the first reaction coil 253 and the second reaction coil 255 are made of stainless steel, to which the resin residue does not adhere.

The resulting vapor enters a first product chamber 254 and a second product chamber 256, respectively. The refrigerant is then condensed by running it first through an air-cooled condenser 261 and then through one or more expansion valves 262. This cooled refrigerant is then supplied to the first product chamber 254 and the second product chamber 256 through a first product coil 258 and a second product coil 260. The first product coil 258 and second product coil 260 condense the vapor back into water, creating purified water that is pumped to the second holding tank 212, using a product pump 268, for use in the wash tank 146 and the rinse tank 168. Refrigerant exiting the first product chamber 254 and the second product chamber 256 may be stored in a reservoir 264 and then supplied to the compressor 251 to close the refrigeration loop. A first reaction chamber sensor 270 and a second reaction chamber sensor 272 indicate water level inside the first reaction chamber 250. A first product chamber sensor 274 and a second product chamber sensor 276 indicate water level inside the first product chamber 254. Signals from these sensors may be advantageously used to control the flow of water and the operation of the system. The second reaction chamber 252 and the second product chamber 256 may be advantageously constructed to have same sensors as described for the first reaction chamber 250 and first product chamber 254.

System Flow Control

Figure 7:
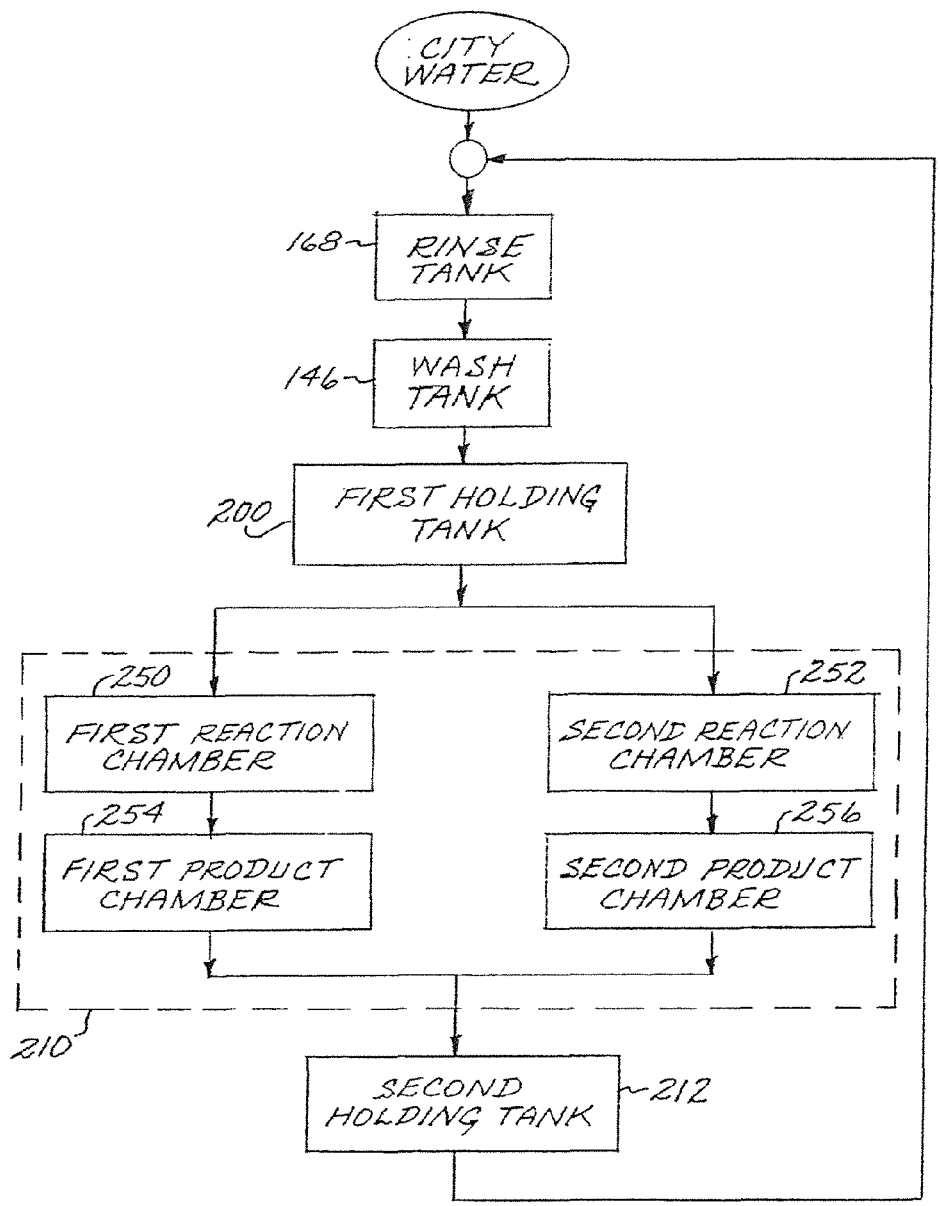
FIG. 7 is a closed loop water flow chart for use with the washing apparatus of FIG. 4.

FIG. 7 shows the closed loop water flow control logic for the exemplary washing apparatus of FIGS. 5A and 5B. Various signals from the sensors are used by PLCs to operate various components of the system. For example, the PLCs can be programmed to operate valves and pumps, based upon a predetermined logic and sensor outputs.

Rinse Tank Flow and Control

If the water level in the rinse tank 168 is at or below a Rinse Tank Operating Low (RTOL) level, and if the water level in the second holding tank 212 is at or above a Second Holding Tank Operating Low (SHTOL) level, the second holding tank outlet valve 225 is opened, and the holding tank pump 214 is started to supply purified water from the second holding tank 212 to the rinse tank 168. If, on the other hand, the water level in the second holding tank 212 is below the SHTOL level, the main valves 226, 228 are opened, and city water is supplied to the rinse tank 168. When the water level in the rinse tank 168 is at or above a Rinse Tank Operating High (RTOH) level, the holding tank pump 214 is stopped, the second holding tank outlet valve 225 and the main valves 226, 228 are closed. If the water level in the rinse tank 168 reaches is at or below a Rinse Tank Low (RTL) level, the rinse tank pump 174 and the heater in the rinse tank 168 are turned-off to avoid cavitation and over-heating of heater elements (not shown). In addition, a "Rinse Tank Low Level" message may be displayed on a visual display device (not shown), and, optionally, an audible alarm (not shown) may be actuated. If the water level in the rinse tank 168 is at or above the Rinse Tank High (RTH) level, the washing apparatus 104 is stopped. In addition, a "Rinse Tank High Level" message may be displayed, and an audible alarm may be actuated. The first rinse tank level sensor 170 can be configured to provide a signal to indicate the RTOL level and the second rinse tank level sensor 172 can be configured to provide a signal to indicate the RTOH level. The first water level sensor 227 of the second holding tank 212 can be configured to provide a signal to indicate the SHTOL level of the second holding tank 212. Similarly, additional sensors in the rinse tank 168 can be configured to provide signals to indicate the RTL level and RTH level.

Wash Tank Flow and Controls

If the water level in the wash tank 146 is at or below a Wash Tank Operating Low (WTOL) level, and if the water level in the rinse tank 168 is at or above RTOL level, the transfer pump 149 is started to transfer water from the rinse tank 168 to the wash tank 146. If the water level in the wash tank 146 is at or above a Wash Tank Operating High (WTOH) level, the transfer pump 149 is stopped. If the water level in the rinse tank 168 is below the RTOL, water is not transferred from the rinse tank 168 to the wash tank 146. If the water level in the wash tank 146 is at or below a Wash Tank Low (WTL) level, the water tank pump 152 and a heater (not shown) in the wash tank 146 are turned-off to avoid cavitation and over-heating of heater elements (not shown). In addition, a "Wash Tank Low Level" message may be displayed, and an audible alarm may be actuated. If the water level in the wash tank 146 is at or above a Wash Tank High (WTH) level, the washing apparatus 104 is stopped. In addition, a "Wash Tank High Level" message may be displayed, and an audible alarm may be actuated. The first wash tank level sensor 148 can be configured to provide a signal to indicate the WTOL level, and the second wash tank level sensor 150 can be configured to provide a signal to indicate the WTOH level signal. Similarly, additional sensors in the wash tank 146 can be configured to provide signals to indicate the WTL level and WTH level.

First Holding Tank

If the water level in the first holding tank 200 is at or below a First Holding Tank Operating Low (FHTOL) level, and if the water level in the wash tank 146 is above the WTOL level, the holding tank pump 198 is started to fill the first holding tank 200. If the water level in the wash tank 146 is below the WTOL level, no action is taken to fill the water into the first holding tank. If the water level in the first holding tank 200 is at or above a first holding tank Operating High (FHTOH) level, the holding tank pump 198 is stopped. If the water level in the first holding tank 200 is at or above a first holding tank high (FHTH) level, a "First Holding Tank High Level" message may be displayed, and an audible alarm may be actuated. If the water level in the first holding tank 200 is at or below a first holding tank Low (FHTL) level, the distillation system 210 is shut-down, and a "First Holding Tank Low Level" message may be displayed, and an audible alarm may be actuated. The first holding tank level sensor 202 can be configured to provide a signal to indicate the FHTOL level, and the second holding tank level sensor 204 can be configured to provide a signal to indicate the FHTOH level signal. Similarly, additional sensors in the first holding tank 200 can be configured to provide signals to indicate the FHTL level and FHTH level.

Distillation System

The distillation system 210 includes the first reaction chamber 250, the second reaction chamber 252, the first product chamber 254, and the second product chamber 256. The operation is described below with respect to the first reaction chamber 250 and the first product chamber 254. The second reaction chamber 252 and second product chamber 256 may be configured to operate in a manner similar to the operation of the first reaction chamber 250 and the first product chamber 254.

If the water level in the first reaction chamber 250 is at or below a first reaction chamber Operating Low (FRCOL) level, first reaction chamber solenoid valve 280 is opened, and water from the first holding tank 200 is pulled into the first reaction chamber 250 under vacuum, through the first holding tank connecting pipe 278. If the water level in the first Reaction Chamber 250 is at or above a first reaction chamber Operating High (FRCOH) level, the solenoid valve 280 is closed, and water flow from the first holding tank 200 to the first reaction chamber 250 is stopped. If the water level in the first reaction chamber 250 is at or above a first reaction chamber High (FRCH) level, vacuum inside the distillation system 210 is released, and the distillation system is powered-off. The first reaction chamber level sensor 270 can be configured to provide a signal to indicate the FRCOL level, and the second reaction chamber level sensor 272 can be configured to provide a signal to indicate the FRCOH level signal. Similarly, additional sensors in the first reaction chamber 250 can be configured to provide signal to indicate the FRCH level.

If the water level in the first product chamber 254 of distillation system is at or above a first product chamber Operating High (FPCOH) level, the product pump 268 is turned on, and water is pumped from the first product chamber 254 to the second holding tank 212 through the second holding tank connecting pipe 284. If the water level in the first product chamber 256 is at or below a first product chamber Operating Low (FPCOL) level, the product pump 268 is turned off, and water flow from the first product chamber 256 to the second holding tank 212 is stopped. If the water level in the first product chamber 254 is at or above a first product chamber High (FPCH) level, vacuum inside the distillation system is released, and the distillation system is powered-off. The first product chamber level sensor 274 can be configured to provide a signal to indicate the FPCOL level, and the second product chamber sensor 276 can be configured to provide a signal to indicate the FPCOH level signal. Similarly, additional sensors in the first product chamber 254 can be configured to provide signal to indicate the FPCH level.

The second reaction chamber 252 and second product chamber 256 may be advantageously constructed to have the same sensors and valves as described above for the first reaction chamber 250 and the first product chamber 254.

Second Holding Tank:

If the water level in the second holding tank 212 is at or below a second holding tank Low (SHTL) level, a "Second Holding Tank Low Level" alarm message may be displayed, and, an audible alauii may be actuated. If the water level in the second holding tank 212 is at or above a second holding tank High (SHTH) level, the distillation system 210 is shut down, and a "Second Holding Tank High Level" alarm message may be displayed, and an audible alarm may be actuated. Additional sensors in the second holding tank 212 can be configured to provide signals to indicate the SHTL level and the SHTH level.

In the preferred embodiment of the present invention, exemplary process parameters and limits are identified below. It should be noted that any suitable process parameters and limits may be used.

| Parameter | Units | Default | Low Limit | High Limit |
| --- | --- | --- | --- | --- |
| Conveyor Speed | Fpm | 1 | 0.5 | 1.5 |
| Wash/Rinse Temperature | F. | 130 | 110 | 140 |
| Wash/Rinse Top Pressure | Psi | 30 | 20 | 40 |
| Wash/Rinse Bottom Pressure | Psi | 10 | 5 | 20 |
| Air Flowrate | Cfm | 500 | 400 | 600 |
| Vacuum Level | Torr | 22 | 10 | 30 |
| Low Pressure | Psi | 100 | 70 | 110 |
| High Pressure | Psi | 300 | 270 | 350 |
| Reaction Chambers Temperature | F. | 80 | 70 | 90 |

Once the wash cycle is completed, the trays 504 are transported to a high powered UV curing station 106 to cure the resin of the items 505. In the UV curing station 106, UV lamps (not shown) are advantageously reciprocated back and forth, exposing the items 505 to short doses of high-intensity UV radiation, instead of a single, long-term dose as is conventionally done. In one embodiment, the UV lamp intensity may be in the range of about 1.5 watts/cm$^2$ to about 3 watts/cm$^2$ and preferably in the range of 2.6 watts/cm$^2$. In another embodiment, the peak wavelength of the UV lamp may be in the range of about 330 nanometers to about 390 nanometers and preferably in the range of 360 nanometers. In one embodiment, the items 505 are exposed to high intensity UV radiation, for about one to three minutes, and preferably for about two minutes. From the UV curing station 106, the trays 504 with the items 505 are transported to a mold and support removal station 107.

The items 505 such as molds are attached to the tray 504 with a sacrificial layer of the cured polymer. The removal station 107 applies sufficient pressure to the items 505 to break the sacrificial layer and separates the items 505 from the trays, without damaging the items 505. The removal station can further include a mechanism to remove any excess sacrificial layer of the cured polymer and provide substantially flat bottom, and presents the items 505 for example, molds for the next process in creating aligners.

The items 505 such as molds are attached to the tray 504 with a sacrificial layer of the cured polymer. The tray 504 further includes multiple thru holes 614, the thru holes 614 corresponding to the location of the items 505 on the tray 504. The diameter of the thru holes 614 may be in the range of about ⅛ inch to about ⅜ inch and preferably about ¼ inch. The removal station 107 includes a detachment station 602, a transfer station 604 and a collection station 606. In the detachment station 602, the item 505 is detached from the tray 504. The tray 504 containing detached items 505 is moved to the transfer station 604 by, for example, a conveyor belt. In the transfer station 604, the items 505 are movably engaged for relative motion with respect to the tray 504 and the items 505 are moved from the transfer station 604 to the collection station 606. In the collection station 606, any remaining sacrificial layer is removed from the items 505 and the items are collected for further processing.

Now, referring to FIG. 9, the tray 504 is received and positioned in the detachment station 602, for the detachment of the items 505 from the tray 504. The detachment station 602 includes a pin plate 608 with a plurality of pins 610. The pin plate 608 is attached to an actuator 612 to move the pin plate 608. The pins 610 of the pin plate 608 are aligned to pass through the thru holes 614 of the tray 504 when the pin plate 608 is moved. The diameter of the pins 610 of the pin plate 608 is selected to be slightly less than the diameter of the thru holes 614 in the tray 504, to permit free movement of the pins 610 through the thru holes 614 of the tray 504.

When the pin plate 608 is moved, the pins 610 enter the thru holes 614 from the bottom of the tray 504, pass through the thru holes 614 of the tray 504 and then engage with the items 505 on the tray 504. After engaging with the items 505, the pin plate 608 is further moved to apply sufficient pressure to the item 505 so as to break the sacrificial layer of the item 505 that is attached to the tray 504. A pressure of about 2 to about 50 psi and preferably about 30 psi is applied to the items 505. The tray 504 is held stationary, when the pin plate 608 is moved. In one embodiment, the movement of the pin plate 608 is limited by a stop (not shown) to prevent excessive penetration of the pins 610 through the tray 504 so as to prevent damage to the item 505. In one embodiment, a cover plate 616 may be positioned on top of the tray 504 so as to confine the movement of the items 505 after the items 505 are detached from the tray 504. In one embodiment, the cover plate 616 may include one or more projections 618 to engage with tray 504 and hold the tray 504 stationary, when the pin plate 608 is moved to detach the item 504 from the tray 505. In one embodiment, the cover plate 616 may be attached to an actuator 620 to move the cover plate 616 to position the cover plate 616 on top of the tray 504, and further engage with the tray 504 and hold the tray 504 stationary, when the pin plate 608 is moved to detach the item 504 from the tray 505. In one embodiment, the underside of the cover plate 616 facing the items 505 may include a layer of compliant material 622, to minimize any damage to the item, if the item 504 strikes the underside of the cover plate 616. For example, a layer of compliant foam like Poron available from DuPont may be used. The thickness of the compliant material may be in the range of about 0.5 inches to 1.5 inches and preferably about one inch.

After the items 505 have been detached from the tray 504 in the detachment station 602, the tray 503 with loose items 505 is moved to the transfer station 604. The transfer station 604 includes a transfer plate 624. The transfer station 604 further includes a transfer mechanism. The transfer mechanism is configured to move the transfer plate 624 in one or more directions. In one embodiment, the transfer mechanism moves the transfer plate 624 toward the tray 504 and the transfer plate 624 engages with the detached item 505 on the tray 504. The transfer plate 624 may include a plurality of pins 628 that are movable. For example, the transfer plate 624 may include a bed of movable pins 628.

The transfer mechanism includes an actuator 650 and a stepper motor 658. The actuator 650 is operable to move an actuator arm 652. The actuator arm 652 is attached to the transfer plate 624 and moves the transfer plate 524 toward and away from the tray, when the actuator is actuated and the actuator arm 652 is moved. The actuator 650 includes a bracket 654 that rests on a rail 656 and the bracket 654 is configured to slide along the rail 656. The stepper motor 658 includes a pulley 670 that rotates when the stepper motor 658 is activated. A belt 670 couples the pulley 670 of the stepper motor 658 to the transfer plate 624 and moves the transfer plate 624 when the stepper motor 658 rotates the pulley 670. When the stepper motor 658 is actuated to move the transfer plate 650, the transfer plate 650 moves along the direction of the rail 656, as the bracket 654 of the actuator 650 slides along the rail 656. The rail 656 is advantageously positioned to run from the transfer station 604 to the collection station 606.

When the transfer plate 624 is moved toward the tray 504, by actuating the actuator 650, the movable pins 628 engage with the items 505 and surround the item 505 by aligning themselves around the contour of the item 505. In one embodiment, the transfer plate 624 is moved close to the tray 504 so as to permit the movable pins 628 to surround the items 505 on the top and the side, but not engage with the surface of the tray 504 in locations where there is no item 504 present. In one embodiment, sufficient downward pressure is maintained on the movable pins 628 to positively maintain the engagement of the movable pins 628 with the item 505 when the movable pins 628 are urged toward the item 505.

Figure 9A:
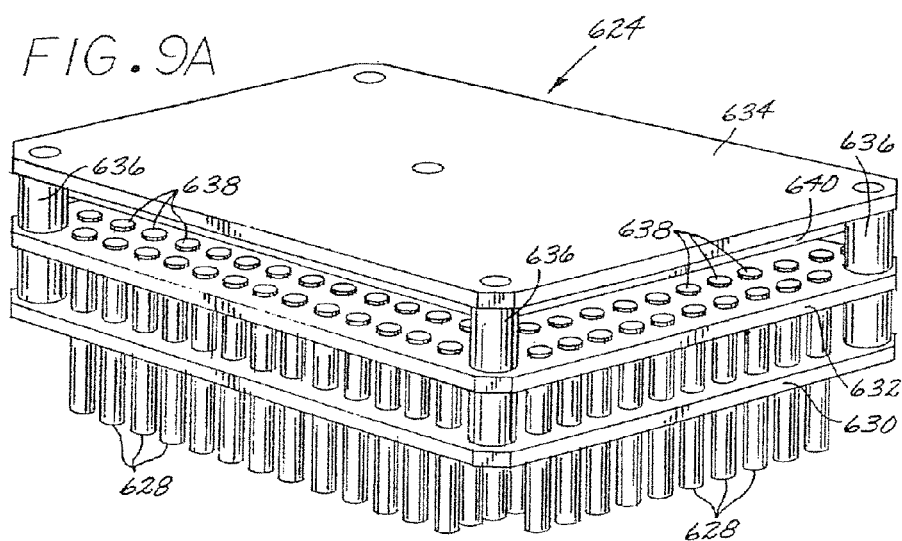
FIG. 9A is a detailed perspective view of a transfer plate for use with the exemplary removal station of FIG. 9.

FIG. 9A shows the transfer plate 624. The transfer plate 624 includes a bottom plate 630, a middle plate 632 and a top plate 634, all spaced apart and held together by a plurality of posts 636. The bottom plate 630 and the middle plate 632 have thru holes that are dimensioned and aligned to permit free movement of the movable pins 628, between a fully extended position and a fully retracted position. The movable pins 628 have heads 538 that are bigger than the thru holes in the middle plate 632 and the middle plate 632 acts as a stop and confines the movement of the movable pin 628 to its fully extended position, when the movable pins 628 frilly extend through the bottom plate 630. The top plate 634 is positioned to limit the movement of the movable pin 628 and act as a stop, when the movable pin 628 is in its fully retracted position. In one embodiment, a portion of the movable pin 628 is at least partially located in the thru hole of the bottom plate 630. The diameter of the movable pins 628 may be in the range of about ⅛ inch to about ⅜ inch and preferably about ¼ inch. In one embodiment, sufficient pressure is applied to the movable pins 628 toward the item, to positively maintain the engagement of the movable pins 628 with the item 505.

In one embodiment, the bottom surface of the top plate 634 may further include a compliant member 640 that imparts downward pressure to the movable pins 628 toward the item 505, when the pins are urged into the compliant member 640, as the movable pins engage with the item 504. In another embodiment, the transfer plate 624 may further include a side plate (not shown) that connects the sides of the top plate 634 and the middle plate 632, to form an enclosure. In one embodiment, the side plate may connect the sides of the top plate 634 and the bottom plate 630 to form an enclosure. The side plate may further include an inlet to receive air under pressure. By injecting air under pressure into the enclosure, a downward pressure can be imparted to the movable pins toward the item 505, to further assist in positive engagement of the items by the movable pins. The air pressure is maintained at such a level to impart sufficient downward pressure to the movable pins 628, while accounting for air leakage through the thru holes in the middle plate and/or bottom plate, if any.

After the transfer plate 624 engages with the item 505, the transfer mechanism moves the transfer plate 624 to the collection station 606. The stepper motor 658 is activated to move the transfer plate 624 toward the collection station 606. As the transfer plate 624 moves to the collection station 606, the items 505 surrounded by the movable pins 628 are moved to the collection station 606. The tray 504 without the item will be further processed in the tray cleaning station 108, which will be described in detail later.

The Collection Station 606 includes a collection plate 642, a debris collector 644 and a finish bin 648. The collection plate 642 includes a plurality of thru holes 646 that open into the debris collector 644. After the transfer plate 624 moves the item 505 over the collection plate 642 of the collection station 606, the transfer mechanism imparts a reciprocating motion to the transfer plate 642, by rotating the stepper motor 658 in both clockwise and counter clockwise direction. The reciprocating motion moves the items 505 relative to the collection plate 642 and breaks any sacrificial layer attached to the item 505. The broken sacrificial layer debris pass through the thru holes 646 of the collection plate 642 and is collected in the debris collector 644 for proper disposal. Then the transfer mechanism moves the transfer plate 624 toward the finish bin 648 by operating the stepper motor 658 and pushes the items 505 into the finish bin 648. After moving the items 505 into the finish bin 648, the transfer mechanism moves the transfer plate 624 to the transfer station 604 by suitably operating the stepper motor 658 and positions the transfer plate 624 in the transfer station 604. The actuator arm 652 is suitably moved by the actuator 650 to position the transfer plate 624 to process the next tray 504 with detached items 505.

The tray 504 without the items is moved to the tray cleaning station 108 to remove any cured resin material that may still remain on the tray 504. For example, a conveyor line or belt may transport a tray 504 that has been processed through the removal station 107 to the tray cleaning station 108.

From the mold and support removal station 107, the trays 504 (without the items) are transported to a tray cleaning station 108 where the tray 504 is cleaned by spraying water at high pressure and high temperature and remove any polymeric resin material that is present on the tray 504. Cleaned trays 504 are inspected and reused for the creation of the items, like the polymeric resin mold items.

Figure 10:
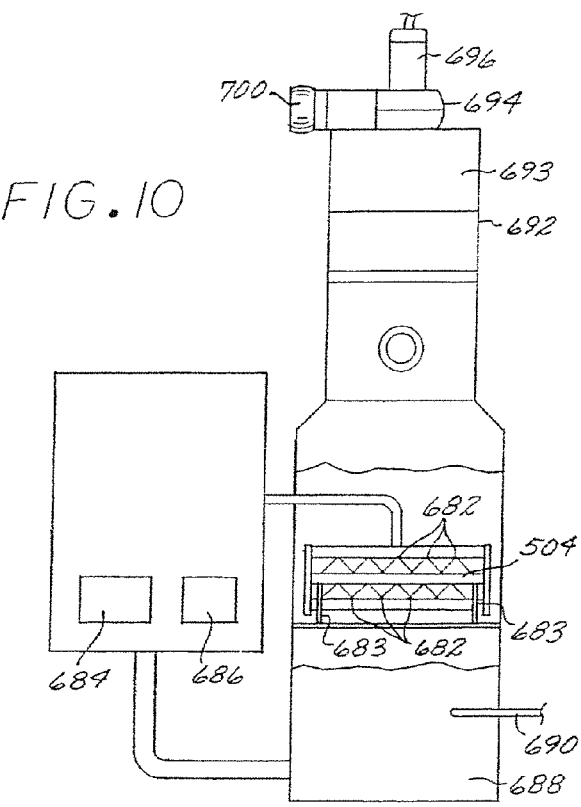
FIG. 10 is a side view of an exemplary cleaning station for use in the system of FIG. 1.

Now referring to FIG. 10, the tray cleaning station 108 includes a water spraying mechanism 680 operable to spray water at elevated temperature and pressure on the tray 504. The water spraying mechanism 680 includes a plurality of nozzles 682 to spray water at a flow rate of about two gallons per minute per nozzle to about eight gallons per minute per nozzle, preferably about four gallons per minute per nozzle and at a pressure of about 1000 psi to 3500 psi, preferably about 3000 psi. Water may be maintained at an elevated temperature, for example, from about 120 degree F. to about 150 degree F., preferably about 140 degree F. Water spraying nozzles 682 are positioned such that water is sprayed on both the top and bottom surface of the tray 504. In one embodiment, a plurality of rows of water spraying nozzles 682 is positioned to spray water on the top surface of the tray 504. Similarly a plurality of rows of water spraying nozzles 682 is positioned to spray water on the bottom surface of the tray 504. The nozzles 682 may be positioned parallel to each other and/or staggered with respect to each other to provide adequate coverage of the tray 504. In one embodiment, the tray 504 may be advantageously moved relative to the water spraying nozzles 682. In one embodiment, a conveyor 683 may move the tray 504 relative to the water spraying nozzles 682, as the water spraying nozzles 682 spray water on the tray. In one embodiment, the conveyor 683 may be of chain type that engages the tray 504 at its edges and moves the tray 504 relative to the water spraying nozzles 682. In another embodiment, the water spraying mechanism 682 may oscillate and spray water on various locations of the tray 504. In yet another embodiment, a combination of the movement of the tray 504 and the movement of the water spraying nozzles 682 may be used.

The water spraying mechanism 680 may further include a motor driven pump 684 with pistons to pressurize the water to the desired pressure before feeding the water to the water spraying nozzles 682. The water spraying mechanism 680 may further include a receiving tank 688 to hold water that will be used to spray on the tray 504 and to collect water that has been sprayed on the tray 504. The receiving tank 688 may further include a heater 690 to heat the water to the desired temperature. The water spraying mechanism 680 may further include a filter 686 connected between the receiving tank and the pump 684, to filter and remove any resin material released from the tray 504 before the water is fed to the pump 684. The water spraying mechanism 680 may include one or more sensors to measure the temperature of the water and the level of water in the receiving tank 688. The sensor outputs may advantageously be used by one or more PLCs to control the water spraying mechanism 680 and the tray cleaning station 108.

The tray cleaning station 108 may further include a steam removal mechanism 692 to remove any water particles mixed with air formed when water at high pressure and high temperature is sprayed on the tray 504. The steam removal mechanism 692 includes a chute 693 attached to a blower 694. The blower 694 is coupled to a motor 696. The blower 694 when operated removes any water particles mixed with air through the chute 693 and the water particles mixed with air is exhausted through the exhaust 700.

After the tray 504 is subjected to high pressure water cleaning, the trays 504 are moved to a tray drying station, where hot air is blown over the trays to remove any residual water remaining on the tray. The tray 504 may be transported through the tray drying station using a conveyor, as air jets flow air over the tray 504. The dried trays 504 may be reused in the creation of items like SLA molds.

In the system for processing polymeric resin items, the movement of the trays 504 containing the items 505 can be automated by using a suitable conventional conveyor system (not shown), of a type well-known in the art. For example, the conveyor system can be configured to move the tray 504 from the unload side 518 of the spin station 507 to the washing station. The conveyor can be configured to move the tray 504 through the various stations. Specifically, referring to FIG. 1, the conveyor system can be configured to move the trays 504 from the spinning station 102 to the washing apparatus 104, from the washing apparatus 104 to the curing station 106, from the curing station 106 to the removal station 107 and from the removal station 107 to the tray cleaning station 108. Within the washing apparatus 104, the conveyor system can be further configured to move the trays 504 from the loading station 110 to the washing station 112, from the washing station 112 to the isolation station 114, from the isolation station to the rinsing station 116, from the rinsing station 116 to the drying station 118, and from the drying station 118 to the unloading station 120. The length of the conveyor system and the speed of the conveyor system can be selected to permit the movement and presentation of the trays 504 to the process stations based upon the cycle time of the process station while minimizing the idle time of the process station waiting for the receipt of a tray 504 to process. If, for example, a subsequent process station has a longer cycle time than the preceding process station, the conveyor length can be extended to add sufficient delay in presenting the tray 504 to the subsequent process station, or the speed of the conveyor station can be varied to ensure no manual intervention is required, and that the tray 504 is presented to the subsequent process station when the latter is ready to receive the tray 504 for processing.

While the present invention is described above with respect to what is currently considered its preferred embodiments, it is to be understood that the invention is not limited to that described above. To the contrary, the invention is intended to cover various modifications and equivalent arrangements within the spirit and scope of the appended claims.

What is claimed is:

1. A method for processing items made of a polymeric resin, wherein the items, in an uncured state, have excess polymeric resin in liquid or semi-liquid form disposed thereon, the method comprising:
   washing the items in the uncured state by spraying water on the items to remove at least some of the excess polymeric resin from the items;
   drying the items with pressurized air;
   rinsing the items by spraying water on the items to remove any remaining excess polymeric resin from the items;
   receiving a mixture of water and polymeric resin removed from the items in the washing and rinsing steps, wherein a part of the polymeric resin in the mixture comprises resin foam;
   allowing the polymeric resin other than the resin foam to settle out of the mixture;
   distilling the mixture of water and resin foam to obtain distilled water; and
   using at least some of the distilled water to spray the items in the washing and rinsing steps.

2. The method of claim 1, wherein the items are disposed on a tray during the washing, drying, and rinsing steps, the method further comprising:
   curing the polymeric resin material of the items on the tray so as to leave the items attached to the tray by a sacrificial layer of cured polymeric resin; and
   detaching the items from the tray by breaking the sacrificial layer of cured polymeric resin.

3. The method of claim 2, wherein the detaching step includes moving the items relative to the tray, whereby a portion of the sacrificial layer remains adhered to the items after detachment.

4. The method of claim 3, further comprising removing from the items the portion of the sacrificial layer adhering to the items after detachment.

5. The method of claim 2, further comprising:
   after detaching the items from the tray, removing the items from the tray; and
   after removing the items from the tray, cleaning the tray of residual cured polymeric resin.

6. A system for processing items made of a polymeric resin, wherein the items, in an uncured state, have excess polymeric resin in liquid or semi-liquid form disposed thereon, the system comprising:
   a washing station operable to remove the excess polymeric resin from the items in the uncured state, the washing station including a water spraying mechanism operable to spray water on the items, the washing station producing a mixture of liquid polymeric resin and water, wherein a part of the liquid polymeric resin in the mixture comprises a resin foam;
   a first holding tank configured to receive the mixture from the washing station, and further configured to allow the liquid polymeric resin other than the resin foam to settle out of the mixture;
   a water distillation system arranged to receive the part of the mixture comprising resin foam from the first holding tank, and operable to distill the part of the mixture comprising resin foam so as to produce distilled water;
   a second holding tank fluidly connected to the water distillation system and the washing station, and configured to receive the distilled water produced by the water distillation system; and
   a pump operable to pump the distilled water from the second holding tank to the washing station.

7. The system of claim 6, further comprising:
   a movable tray on which the items are carried to the washing station in an uncured state;
   a curing station operable to cure the items, leaving the cured items attached to the tray by a sacrificial layer of cured polymeric resin; and
   a detachment station operable to detach the items from the tray by breaking the sacrificial layer of cured polymer resin.

8. The system of claim 7, wherein the detachment station includes an item-engaging apparatus operable to break the sacrificial layer of cured polymeric resin by an application of pressure to the items.

9. The system of claim 8, wherein the tray has a plurality of apertures, and wherein the item-engaging apparatus includes a plurality of pins that are moveable relative to the tray so as to engage the items though the apertures in the tray with a pressure sufficient to break the sacrificial layer of cured polymeric resin.

10. The system of claim 7, further comprising a transfer station including a transfer plate that is operable on the items after detachment from the tray to impart a motion to the items that removes from the items debris including any cured polymeric resin from the sacrificial layer that remains on the items after detachment of the items from the tray.

11. The system of claim 10, further comprising:
    a collection station operable to remove the detached items from the tray; and
    a cleaning station operable to remove cured polymeric resin attached to the tray after removal of the items therefrom.

12. The system of claim 6, wherein the distillation system comprises:
    a reaction chamber operable to maintain vacuum and having a heating coil operable to separate the resin foam from the water in the mixture by evaporating the water, wherein the heating coil has a surface that is not conducive to adhesion of the liquid polymeric resin during the separation; and
    a condensation chamber operably connected to the reaction chamber so as to receive water vapor from the reaction chamber and operable to condense the water vapor into liquid water.

* * * * *